(12) United States Patent
Nagy et al.

(10) Patent No.: US 11,210,918 B2
(45) Date of Patent: Dec. 28, 2021

(54) TAMPER RESISTANT ONE-TIME USE WRISTBAND AND CLASP AND ALGORITHM TO ENHANCE THE PRACTICAL USE OF RADIO FREQUENCY FOR PROXIMITY BETWEEN TWO OR MORE ENTITIES

(71) Applicant: Invisalert Solutions, Inc., West Chester, PA (US)

(72) Inventors: Peter Nagy, Newtown Square, PA (US); Michele Marcolongo, Aston, PA (US); Regina Widdows, Ivyland, PA (US); Jonathan D. Albert, Philadelphia, PA (US); Eric Chang, Philadelphia, PA (US); Jason Zerweck, Philadelphia, PA (US)

(73) Assignee: Invisalert Solutions, Inc., West Chester, PA (US)

( * ) Notice: Subject to any disclaimer, the term of this patent is extended or adjusted under 35 U.S.C. 154(b) by 0 days.

(21) Appl. No.: 17/152,769

(22) Filed: Jan. 19, 2021

(65) Prior Publication Data

US 2021/0166544 A1    Jun. 3, 2021

Related U.S. Application Data

(63) Continuation of application No. 16/344,506, filed as application No. PCT/US2017/051545 on Sep. 14, 2017, now Pat. No. 10,896,590.

(Continued)

(51) Int. Cl.
*G08B 21/02* (2006.01)
*H04B 17/318* (2015.01)
(Continued)

(52) U.S. Cl.
CPC ............ *G08B 21/02* (2013.01); *G01S 5/0284* (2013.01); *G01S 13/751* (2013.01); *G16H 10/65* (2018.01); *G16H 40/20* (2018.01); *H04B 17/318* (2015.01)

(58) Field of Classification Search
CPC .................................................... G08B 21/02
See application file for complete search history.

(56) References Cited

U.S. PATENT DOCUMENTS 5,218,344 A    6/1993 Ricketts
6,225,906 B1    5/2001 Shore
(Continued)

FOREIGN PATENT DOCUMENTS

WO    WO02/082348 A2    10/2002

OTHER PUBLICATIONS

Consumer Cellular; Huawei 8652—managing contacts; 1 page (Screenshot); retrieved from the internet (https://www.youtube.com/watch?v=oCazslu6NLg on Sep. 17, 2012.

(Continued)

*Primary Examiner* — Travis R Hunnings
(74) *Attorney, Agent, or Firm* — Shay Glenn LLP

(57) ABSTRACT

An electronic patient monitoring system and method of operation that includes one or more generally non-metal, tamper-resistant patient identification and monitoring devices, an observer transmitter/receiver device configured to receive and detect one or more beacon signals that exceed a predetermined threshold from at least one of the not easily removable patient identification and monitoring devices, set a time to hold open a window for a response on the transmitter/receiver device, and send a request for information to the observer with the transmitter/receiver device, and a central computer system. Each of the transmitter/receiver device and the central computer system, including, at least, (Continued)

a computer processor, communications components and system software to communicate with the observer transmitter/receiver device at specified/predetermined time intervals to receive observer- and patient-specific information.

20 Claims, 26 Drawing Sheets

Related U.S. Application Data

(60) Provisional application No. 62/394,637, filed on Sep. 14, 2016.

(51) Int. Cl.
*G16H 40/20* (2018.01)
*G16H 10/65* (2018.01)
*G01S 5/02* (2010.01)
*G01S 13/75* (2006.01)

(56) References Cited

U.S. PATENT DOCUMENTS

| | | |
|---|---|---|
| 6,406,426 B1 | 6/2002 | Reuss et al. |
| D507,798 S | 7/2005 | Jewitt et al. |
| 6,954,148 B2 | 10/2005 | Pulkkinen et al. |
| 7,154,397 B2 | 12/2006 | Zerhusen et al. |
| 7,242,306 B2 | 7/2007 | Wildman et al. |
| 7,382,247 B2 | 6/2008 | Welch et al. |
| D577,364 S | 9/2008 | Flynt et al. |
| 7,450,015 B2 | 11/2008 | Singer et al. |
| D588,152 S | 3/2009 | Okada |
| D588,153 S | 3/2009 | Okada |
| 7,541,935 B2 | 6/2009 | Dring et al. |
| 7,570,152 B2 | 8/2009 | Smith et al. |
| D599,363 S | 9/2009 | Mays |
| D607,001 S | 12/2009 | Ording |
| 7,642,290 B2 | 1/2010 | Kaplan |
| D614,641 S | 4/2010 | Viegers et al. |
| 7,764,167 B2 | 7/2010 | Reeves et al. |
| 7,825,794 B2 | 11/2010 | Janetis et al. |
| D643,436 S | 8/2011 | Lemay |
| D656,157 S | 3/2012 | Khan et al. |
| D656,503 S | 3/2012 | Brierley et al. |
| D682,262 S | 5/2013 | Akana et al. |
| 8,605,094 B1 | 12/2013 | Alfaro et al. |
| D701,229 S | 3/2014 | Lee |
| D701,521 S | 3/2014 | Kim et al. |
| D715,820 S | 10/2014 | Rebstöck |
| D718,779 S | 12/2014 | Hang Sik et al. |
| D720,766 S | 1/2015 | Mandal et al. |
| D724,603 S | 3/2015 | Williams et al. |
| 8,984,436 B1 | 3/2015 | Tseng et al. |
| D765,110 S | 8/2016 | Liang |
| D789,956 S | 6/2017 | Ortega et al. |
| D797,133 S | 9/2017 | Marcolongo et al. |
| D820,850 S | 6/2018 | Tekamp et al. |
| D866,586 S | 11/2019 | Suter et al. |
| 10,482,753 B2 * | 11/2019 | Nelson ............... G08B 21/245 |
| D873,278 S | 1/2020 | Nakahara et al. |
| D906,359 S | 12/2020 | Nagy et al. |
| 10,896,590 B2 | 1/2021 | Nagy et al. |
| 2002/0060630 A1 | 5/2002 | Power |
| 2002/0196147 A1 | 12/2002 | Lau |
| 2005/0094205 A1 | 5/2005 | Lo et al. |
| 2007/0118813 A1 | 5/2007 | Forstall et al. |
| 2007/0129983 A1 | 6/2007 | Scherpbier et al. |
| 2007/0267475 A1 | 11/2007 | Hoglund et al. |
| 2008/0012767 A1 | 1/2008 | Caliri et al. |
| 2008/0015903 A1 | 1/2008 | Rodgers |
| 2008/0027288 A1 | 1/2008 | Renz |
| 2009/0075694 A1 | 3/2009 | Kim et al. |
| 2009/0299827 A1 | 12/2009 | Puri et al. |
| 2010/0026510 A1 | 2/2010 | Kiani et al. |
| 2010/0066541 A1 | 3/2010 | Craine |
| 2010/0090971 A1 | 4/2010 | Choi et al. |
| 2010/0201821 A1 | 8/2010 | Niem et al. |
| 2010/0217618 A1 | 8/2010 | Piccirillo et al. |
| 2010/0249540 A1 | 9/2010 | Lisogurski |
| 2010/0253521 A1 | 10/2010 | Williams, Sr. et al. |
| 2011/0082808 A1 | 4/2011 | Beykpour et al. |
| 2011/0105854 A1 | 5/2011 | Kiani et al. |
| 2011/0179387 A1 | 7/2011 | Shaffer et al. |
| 2011/0191124 A1 | 8/2011 | Sung et al. |
| 2011/0197163 A1 | 8/2011 | Jegal et al. |
| 2012/0095822 A1 | 4/2012 | Chiocchi |
| 2012/0154582 A1 | 6/2012 | Johnson et al. |
| 2012/0184207 A1 | 7/2012 | Gaines et al. |
| 2013/0018673 A1 | 1/2013 | Rubin |
| 2013/0132908 A1 | 5/2013 | Lee et al. |
| 2013/0218583 A1 | 8/2013 | Marcolongo et al. |
| 2013/0227486 A1 | 8/2013 | Brinda |
| 2014/0067770 A1 | 3/2014 | Cheong et al. |
| 2014/0189608 A1 | 7/2014 | Shuttleworth et al. |
| 2014/0283142 A1 | 9/2014 | Shepherd et al. |
| 2015/0084769 A1 * | 3/2015 | Messier ............. G08B 21/0446 340/539.13 |
| 2015/0242665 A1 | 8/2015 | Antonescu et al. |
| 2016/0026837 A1 | 1/2016 | Good et al. |
| 2016/0078752 A1 | 3/2016 | Vardi |
| 2016/0109853 A1 | 4/2016 | Kobayashi |
| 2016/0253470 A1 * | 9/2016 | Marcolongo .......... G16H 80/00 705/2 |
| 2017/0116560 A1 | 4/2017 | Wickstrom et al. |
| 2017/0243056 A1 | 8/2017 | Cheng et al. |
| 2019/0043337 A1 | 2/2019 | Liu et al. |
| 2019/0146550 A1 | 5/2019 | Berardinelli |

OTHER PUBLICATIONS

Contacts Like Listview: Contacts like listview—stack overflow; 1 page; retrieved from the internet (http://stackoverflow.com/questions/5017080/contacts-like-listview) on Feb. 16, 2011.

invisalertsolutions.com; 15-minute checks psychiatry inpatient setting; Feb. 16, 2016; 2 pages retrieved from the internet (https://www.invisalertsolutions.com/>(year:2018); on Aug. 18, 2020.

Google Drive Blog; Rapid wireframe sketching in google docs; 2pages; retrived from the internet (https://drive.googleblog.com/2010/05/rapid-wireframe-sketching-in-google-docs.htm) on May 2010.

Java; How to add my app icon in contact list of users' android phone—stack overflow; 1 pages retrieved from the internet (https:stackoverfiew.com/questioris/25029855/how-to-add-my-app-icon-in-contact-list-of-users-android-phone) on Aug. 18, 2020.

McNickle; 7 E-Health tools to get patients engaged; 5 pages; retrieved from the internet (http://www.informationweek.eom/healthcare/patient-tools/7-e-health-tools-to-get-patients-engaged/d/d-id/1106716) on Oct. 8, 2012.

Pandey; [How-to] Backup your phone contacts to google; 1 page (Screenshot); retrieved from the interent (http://www.youtube.com/watch?v=vZwvc-7CCf4) on Nov. 15, 2012.

Sain Lukes College on Google Play Reviews; Similar play app stats; 1 page; retrived from the internet (https://www.similarplay.com/dublabs/saint_lukes_college/apps/com.dud.app.saintlukes) on Aug. 18, 2020.

Vladleevideo; Quick Contacts for Android, 2 pages (Screenshot); retrieved from the internet (https://www.youtube.com/watch?v=iRn97Neh-cY) on Apr. 18, 2017.

Winarno; Howto backup contacts on Samsung S4; 1 page (Screenshot); retrieved from the internet (https://www.youtube.com/watch?v=_MN9RbuV9Vc>); on Jul. 7, 2014.

Marcolongo et al.; U.S. Appl. No. 29/550,879, entitled "Graphical user interface for display screen or portion thereof," filed Jan. 7, 2016.

* cited by examiner

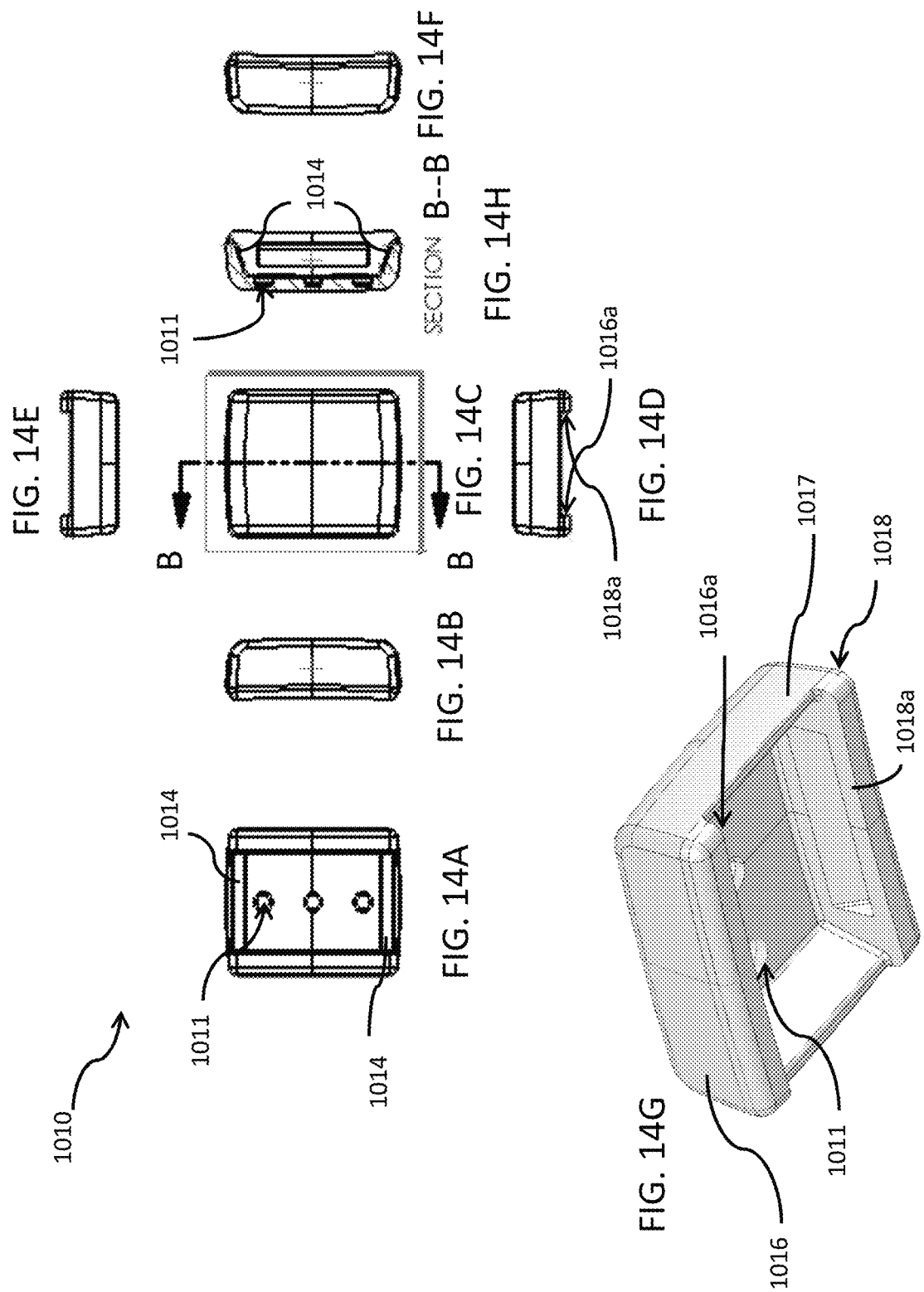

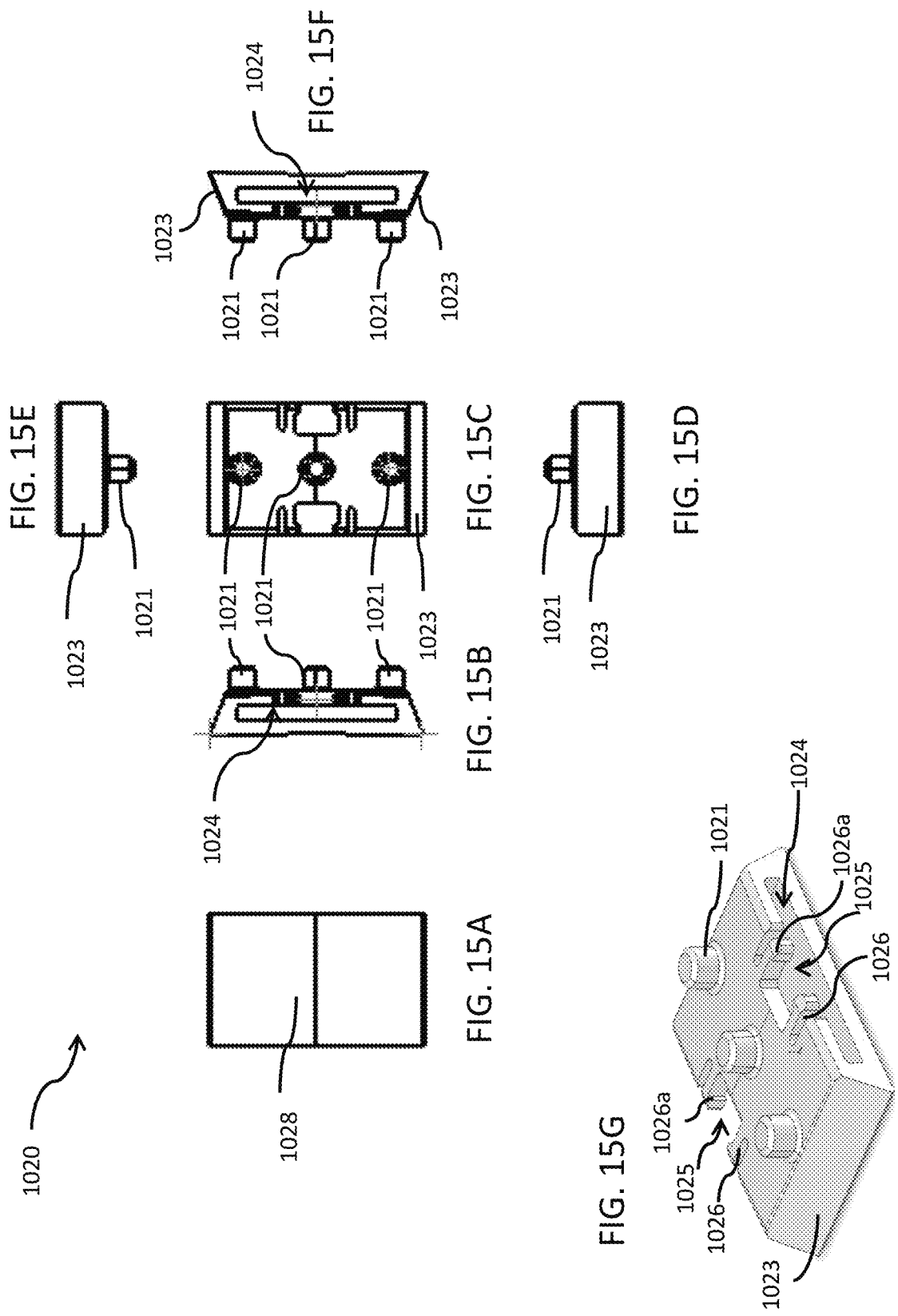

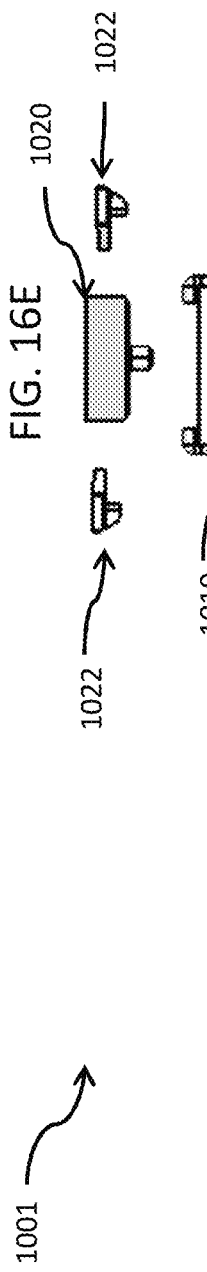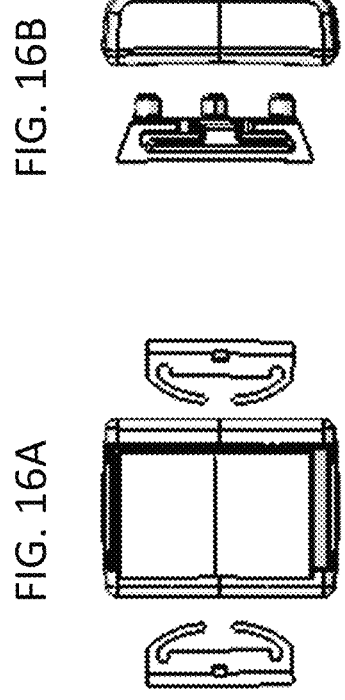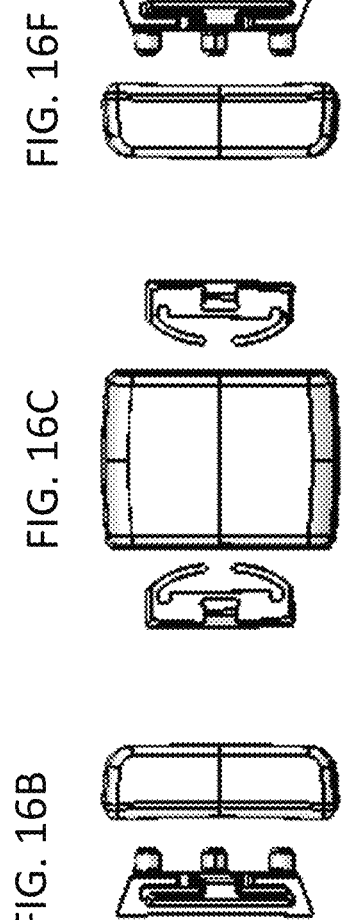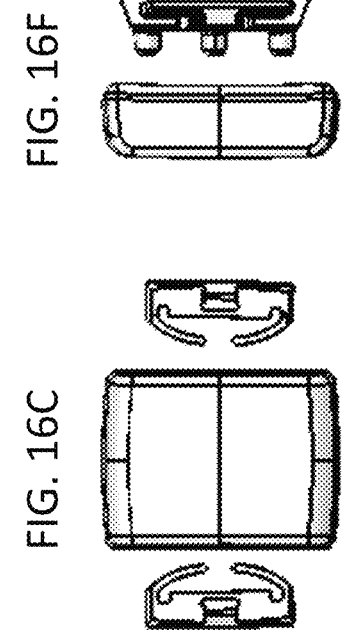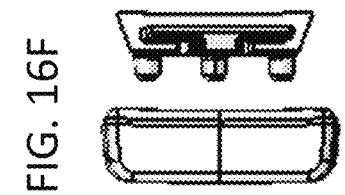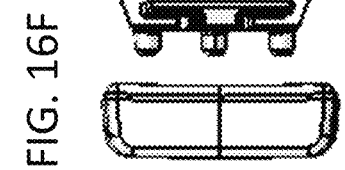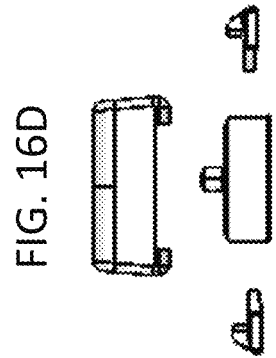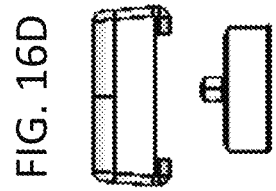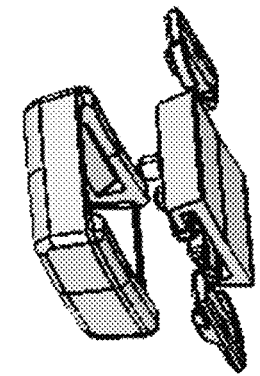

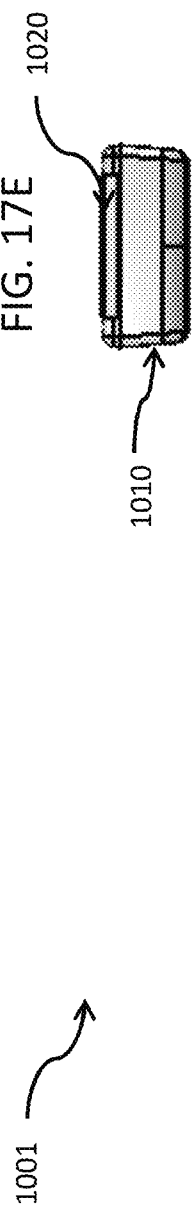
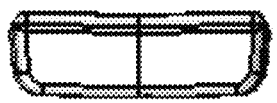
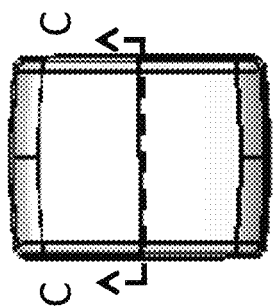
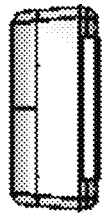
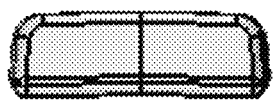
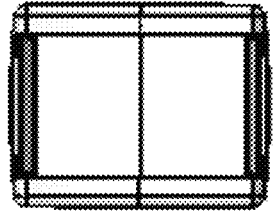
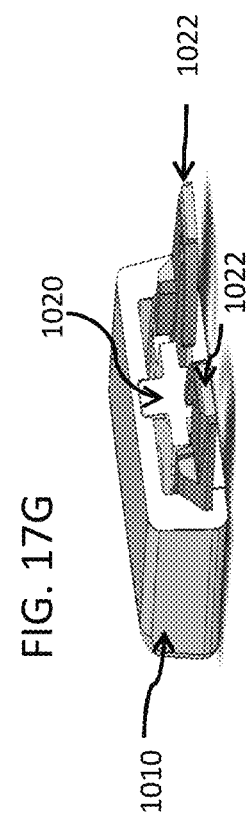

RFID signal strength of a wrist worn beacon as a function of distance from the beacon.

Person one using an iPad with an RF receiver to determine proximity to person two wearing a wearable beacon or device with an RF transmitter broadcasting a signal.

FIG. 19
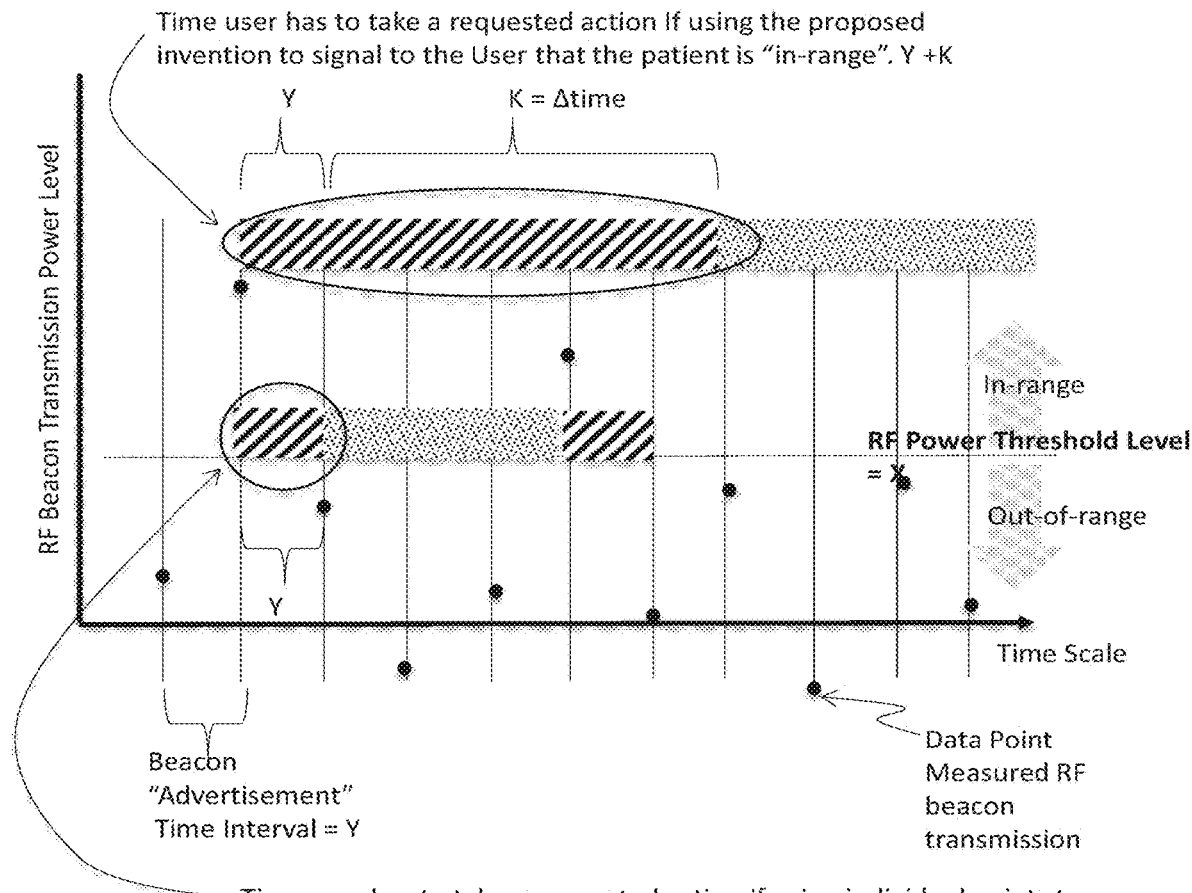
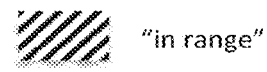 "in range"
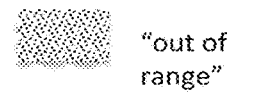 "out of range"
Graphic illustrates how much time a user has to respond to a software request for some action driven by a trigger.

FIG. 25
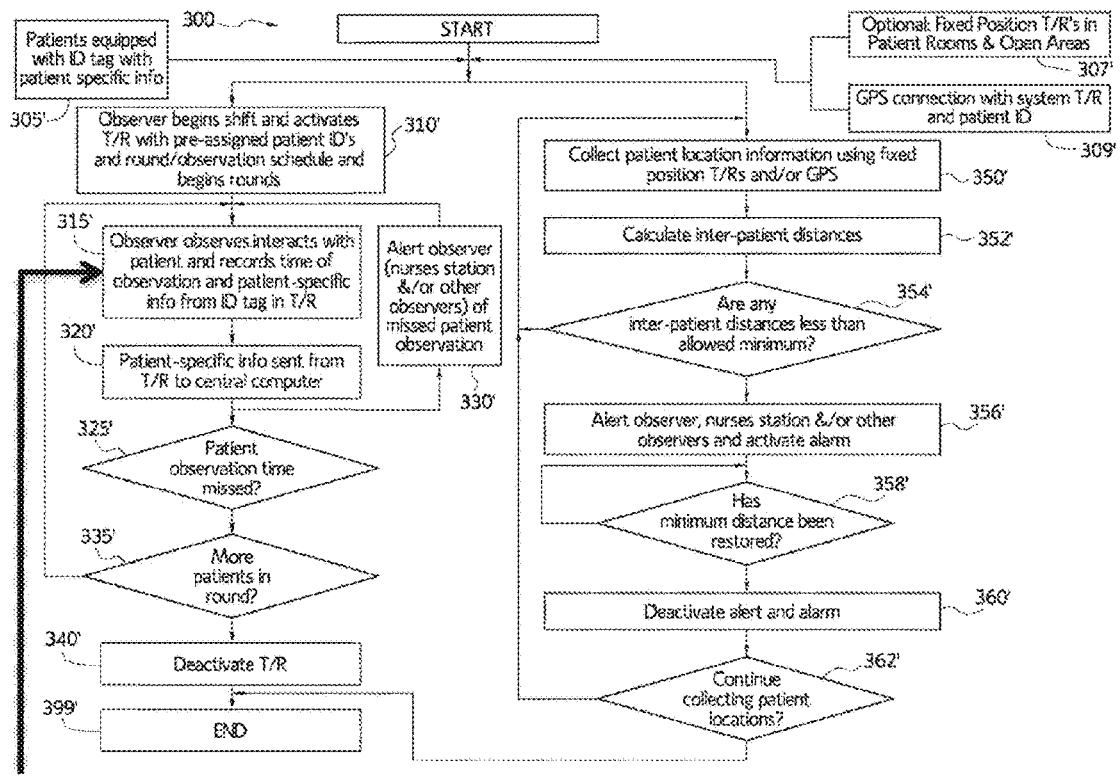
Staff observes/interacts w/ Patient IF tablet application software prompts the staff (user) that the patient is 'in'range' or not 'in-range' via a visual or audio or combination of indicators.
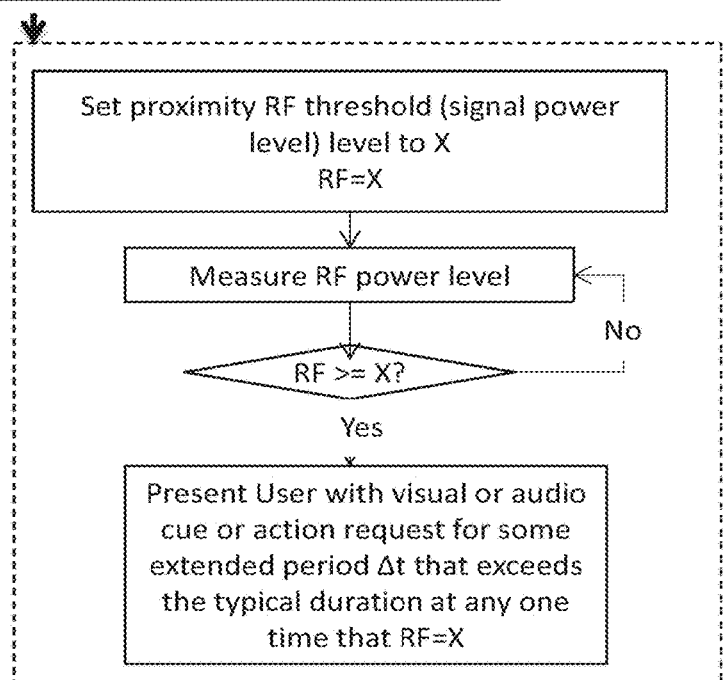

TAMPER RESISTANT ONE-TIME USE WRISTBAND AND CLASP AND ALGORITHM TO ENHANCE THE PRACTICAL USE OF RADIO FREQUENCY FOR PROXIMITY BETWEEN TWO OR MORE ENTITIES

CROSS REFERENCE TO RELATED APPLICATIONS

This application is a continuation of U.S. patent application Ser. No. 16/344,506, filed Apr. 24, 2019, titled "TAMPER RESISTANT ONE-TIME USE WRISTBAND AND CLASP AND ALGORITHM TO ENHANCE THE PRACTICAL USE OF RADIO FREQUENCY FOR PROXIMITY BETWEEN TWO OR MORE ENTITIES," now U.S. Pat. No. 10,896,590, which is a national phase application under 35 USC 371 of International Patent No. PCT/US2017/051545, filed Sep. 14, 2017, titled "TAMPER RESISTANT CLASP AND WRISTBAND APPARATUS AND ASSOCIATED PATIENT MONITORING SYSTEM AND METHOD OF USE," now International Publication No. WO2018/053116, which claims the benefit of U.S. Provisional Patent Application No. 62/394,637, filed Sep. 14, 2016, and titled "TAMPER RESISTANT ONE-TIME USE WRISTBAND AND CLASP AND ALGORITHM TO ENHANCE THE PRACTICAL USE OF RADIO FREQUENCY FOR PROXIMITY BETWEEN TWO OR MORE ENTITIES."

TECHNICAL AREA

The disclosed subject matter is in the field of patient monitoring systems to ensure patient safety. The disclosed subject matter more particularly relates to a tamper resistant clasp and wristband with an associated beacon and patient monitoring systems and improved methods of signal recognition and processing. In general, the systems have one or more assigned facility staff members that actively monitor, i.e., directly observe, patients under their care that are wearing the tamper resistant clasp and wristband at specific time intervals to ensure the patients are engaging in safe behaviors and participating in the therapeutic milieu.

BACKGROUND

Individuals are often in need of secure placement in a healthcare facility to ensure that their safety and the safety of others within the community will be maintained. When an individual is unable to care for him/herself due to physical or mental disability or, for example, the individual is unable to commit to maintain his/her own safety, or has made an attempt to end his/her life, inpatient psychiatric care is suggested. Although the description below relates to psychiatric care, the system and method are equally applicable to patients without psychiatric issues, but with physical issues.

Inpatient psychiatric care is appropriate for individuals who are voicing suicidal ideation and have expressed a specific and feasible plan as to how they may successfully complete a suicide attempt. Likewise, inpatient care is appropriate for individuals who have recently attempted suicide or made a serious suicidal gesture. Inpatient care is the appropriate course of treatment for individuals who are voicing homicidal ideation, precipitated by a diagnosed psychiatric condition or as specified by an outpatient physician according to his/her diagnosis and treatment strategy. Inpatient psychiatric care may also be appropriate for individuals who are unable to refrain from self-harm such as excessive cutting behaviors or self-mutilation. Inpatient psychiatric care is appropriate for individuals who are unable to care for themselves due to a diagnosed psychiatric disorder which interferes with their ability to function effectively.

Inpatient psychiatric care typically consists of a free standing or hospital affiliated facility that is dedicated to the treatment of a primary psychiatric disorder. Inpatient psychiatric facilities consist of locked, secured units which may serve a general adult population or be specialized to a specific patient demographic such as adolescent, older adult, or patients with a dual diagnosis which would include a psychiatric diagnosis concurrent with a substance abuse issue.

Inpatient units are locked facilities and patients do not have free access to enter or leave the unit and do not have access to some restricted areas on the unit. The inpatient unit environment is a secured setting where careful consideration has been taken to ensure most potentially hazardous environmental objects have been removed. Obvious objects of risk have been removed to lessen the potential for patients harming themselves. Upon entering an inpatient facility all patient belongings are examined for items that could be potentially harmful. Any sharp or potentially harmful items are confiscated and placed in a secure area for use with direct staff supervision.

The physical environment of the unit has been adapted to ensure maximum safety for the patients and staff. Shower rods and shower heads do not bear weight, light fixtures are recessed, cameras monitor common areas throughout the unit.

Despite these adaptations, certain risk factors are inherent in the configuration of any inpatient psychiatric unit, and it would be impossible and inhumane to remove any and all potentially harmful items.

Given this inherent risk and the need to ensure patient safety, inpatient psychiatric units closely observe all patients at specified time intervals. The specified observation period is determined by qualified mental health professionals and may be modified dependent on the risk factors that the patient is exhibiting. The highest level of observation would be a 1:1 observation status with a staff person assigned to monitor the patient's activities. The staff person typically needs to be within arm's length of the patient and is not permitted to be assigned any other unit responsibilities. The next level of observation is an eyesight status, wherein the staff member needs to maintain visual contact at all times to monitor all of a patient's activities.

As used herein, "Visual Observation" is defined as the observation made by an observer visually to determine the activity of the patient; and "Line-of-Sight" is defined as an electronic connection from the observer to the patient which, generally, is effectively made without obstacles in the path of the signal.

Excluding these higher levels of continuous observation, all other observation checks relate to specified time intervals. The attending physician, or other qualified mental health professional, predetermines what specified time period would best suit the patient's needs for safety. This specified time interval is shared with the unit staff member (s) that are responsible for monitoring the patients. The specified time interval for the observation check to ensure patient safety may be visually observed every 15 minutes, 30 minutes, 1 hour, etc. depending on the clinical needs of the specific patient.

When completing an observation check for a patient, a staff member is required to make rounds on the unit to ensure that the patients assigned to their care are engaged in safe behaviors. The staff member is required to personally witness, through a visual observation what each patient is doing (e.g., attending group therapy, sleeping, etc.), and document that this observation check was completed.

Currently, these observation checks are manually documented by unit staff member(s), who document this information on a clipboard that holds the paper observation checklist. This observation checklist specifies where the patient is on the unit, and includes the initials of the staff member that verified the patient(s) was/were visually observed for engagement in safe behavior at the specified time interval.

The current system presents many opportunities for human error, which welcomes risk for patient safety. With the current system, the unit observation clipboard may have numerous (for example 15, 25 or more) separate observation documents. There may be numerous different observers assigned to a psychiatric unit at one time, depending on the size of the unit as well as the observer to patient ratios specified by the facility. It is very challenging for staff to accurately ensure that each patient has been appropriately monitored without repeatedly assessing all of these paper documents.

With the current system, it is possible to incorrectly identify patients. A staff member may observe patients who are attending a group therapy session. By glancing in the group therapy room, a staff person may make the assumption that all of the patients on the unit are in attendance, when in fact one or more patients may have excused themselves from the group and may be engaged in unsafe behaviors.

In addition, staff may be unsure of each patient's name on a unit. On a unit with numerous patients it is difficult for a staff person coming on duty to verify each individual's name, and match it to the specific observation checklist specific to that patient on the clipboard. Errors often occur when a staff member makes an assumption based on patient demographics (e.g., age, sex, name, room number, etc.) versus primary verification methods (e.g., checking wristband).

The current system allows the potential for documentation that all patients on the unit had been visually observed as scheduled, when in fact, an observation check may have been missed. In theory, staff could be non-conformant with protocol by documenting that all visual observations had been completed, on schedule, without leaving the nurses' station, or without being on the unit and performing the required visual assessment.

Unfortunately, with the current system, when a visual observation check is missed or erroneously recorded there is no mechanism to alert the staff member or unit personnel that the observation check was missed or incorrect. Typically, a missed or undocumented observation is discovered after the fact, upon review of the paper documentation, or upon discovery of an adverse patient event. The charge nurse or unit manager would not be immediately aware that visual observation checks were being missed as there is no mechanism for real time notification.

BRIEF DESCRIPTION OF THE DRAWINGS

Non-limiting and non-exhaustive embodiments of the presently disclosed subject matter are described with reference to the following figures, wherein like reference numerals and/or indicia refer to like parts throughout the various views unless otherwise precisely specified.

FIGS. 14A-14H include top, bottom, back side, left side, right side, front side views and a top perspective view of the clasp top body portion along line B-B of the clasp of FIGS. 10 & 11, in accordance with an embodiment of the disclosed subject matter.

FIGS. 15A-15G include top, bottom, back side, left side, right side, front side views and a top perspective view of the clasp bottom body portion of the clasp of FIGS. 10 & 11, in accordance with an embodiment of the disclosed subject matter.

FIGS. 16A-16G include top, bottom, back side, left side, right side, front side exploded views and a top perspective view of the clasp portion of FIGS. 10 & 11, in accordance with an embodiment of the disclosed subject matter.

FIGS. 17A-17G include top, bottom, back side, left side, right side, front side views and a top perspective, cross-sectional view along line C-C of the clasp portion of FIGS. 10 & 11, in accordance with an embodiment of the disclosed subject matter.

FIG. 19 is a timeline showing the time a user has to respond to a software request received as a result of the proximity of a beacon and associated clasp to a user with a mobile sensor device of FIGS. 10 & 11, in accordance with an embodiment of the disclosed subject matter.

FIG. 25 is a flow chart illustrating the process from FIG. 3b that is followed by an observer using an electronic patient monitoring system with GPS and inter-patient distance monitoring showing where an electronic patient monitoring system and decision making process can be implemented in the process, in accordance with an embodiment of the disclosed subject matter.

DETAILED DESCRIPTION

One or more embodiments of the disclosed subject matter include (i.e., comprise) a system that uses active radio frequency (RF) identification (RFID) technology to assess completion of, for example, but not limited to, visual monitoring of patients in a psychiatric unit of a treatment center or hospital. There are several main components to the visual monitoring system, a patient identification device with a beacon that emits a patient-specific signal, an observer transmitter/receiver (T/R) with specialized beacon signal detection and processing capabilities that improve T/R system performance and a centralized software program for data storage, monitoring and retrieval. Together, this system allows for visual observations of patients in an ethically responsible manner, while allowing for increased observation compliance from the current paper checklist system commonly employed. Other embodiments of the disclosed subject matter can also include multiple fixed-position T/Rs that are permanently affixed to walls or other structural features of the facility in predetermined positions. In other embodiments the beacons in the identification devices can be configured to also receive and then retransmit the received signals. The received signals can originate from other identification device beacons, as well as any T/R or any computer in the system and the retransmitted signals can go to still other identification device beacons, T/Rs and other computers in the system. This can be used to implement a mesh networking system, such as, for example, but not limited to, a Bluetooth mesh network, which has been defined in a Bluetooth Mesh Profile Specification and a Bluetooth Mesh Model Specification on the Bluetooth website.

This application claims priority to U.S. Provisional Application Ser. No. 62/394,637, filed Sep. 14, 2016, which is hereby incorporated by reference herein in its entirety.

Figure 1A:
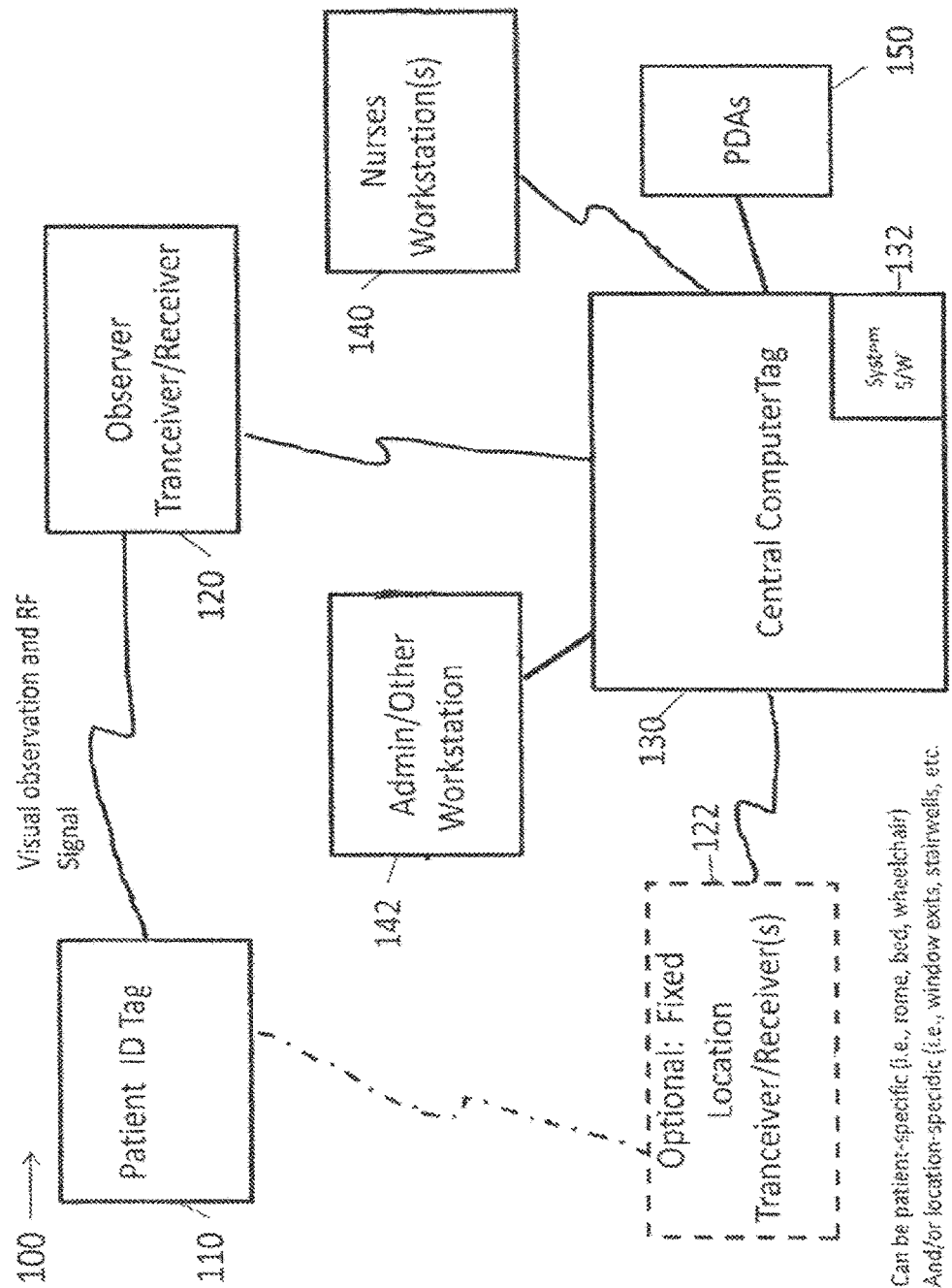
FIG. 1a is a block diagram of an electronic monitoring system using visual observation and radio frequency (RF) signals, in accordance with an embodiment of the disclosed subject matter.

FIG. 1a is a block diagram of an electronic monitoring system using visual observation and RF signals, in accordance with an embodiment of the disclosed subject matter. In FIG. 1a, an electronic monitoring system 100 is illustrated that includes an active patient identification (ID) tag 110 that is connectible by radio frequency communication during visual observation with a generally mobile observer transceiver/receiver (T/R) 120 which serves as a power source and activates the active patient ID tag 110 and is communicatively connected to a central computer system 130 that has an electronic monitoring system software program 132 installed and running. The electronic monitoring system 100 may optionally include one or more fixed location T/Rs 122 that is/are also connectible by radio frequency during visual observation to and also serve(s) as a power source to activate the patient identification tag 110. Each fixed location T/R 122 is communicatively connected to the central computer system 130 and the electronic monitoring system software program 132. One or more workstations, for example, one or more nurses workstations 140 and/or one or more administrative/administrator or other workstations 142 may be locally and/or remotely connected to the central computer system 130 and the electronic monitoring system software program 132. In addition, one or more PDA devices 150 may be directly or wirelessly connected to and access the electronic monitoring system software program 132. The software program 132 will take the transmitted data and convert it to a digital display that shows, for example, the patient identification, observation time, patient activity and the personal identification of the staff member who made the visual observation. The digital display can be displayed on the observer's handheld device as well as on the workstation and/or PDA tracking screens. If a scheduled visual observation check is missed, an alarm (visual or by sound, for example) will appear on the screen of the observer and at any workstation and/or PDA, such as a nurse's workstation 140. The system software 132 will also keep a permanent record of all observation histories that can be downloaded to an archival database on a secure hospital server.

Patient Identification System. Using RFID or similar technology (e.g., infra-red, Bluetooth, low-energy Bluetooth, etc.), patient information including name, room number and other relevant information is stored in a passive or an active RFID electronic tag unique to and substantially continuously attached to the patient through one of several means. The tag can be attached to or implanted in a wristband worn by the patient. The tag can be a rigid chip or a flexible circuit board. Flexible circuit boards can be custom designed for the active signal and patient information storage using standard state-of-the-art technology. The tag can also be attached or embedded in a garment or other tag or device worn, attached to or used by the patient. Some of the devices in which the tag can be located can include, but are not limited to, a helmet, a prosthetic device, a brace, a walker, a wheelchair, a necklace, etc.

Figure 1B:
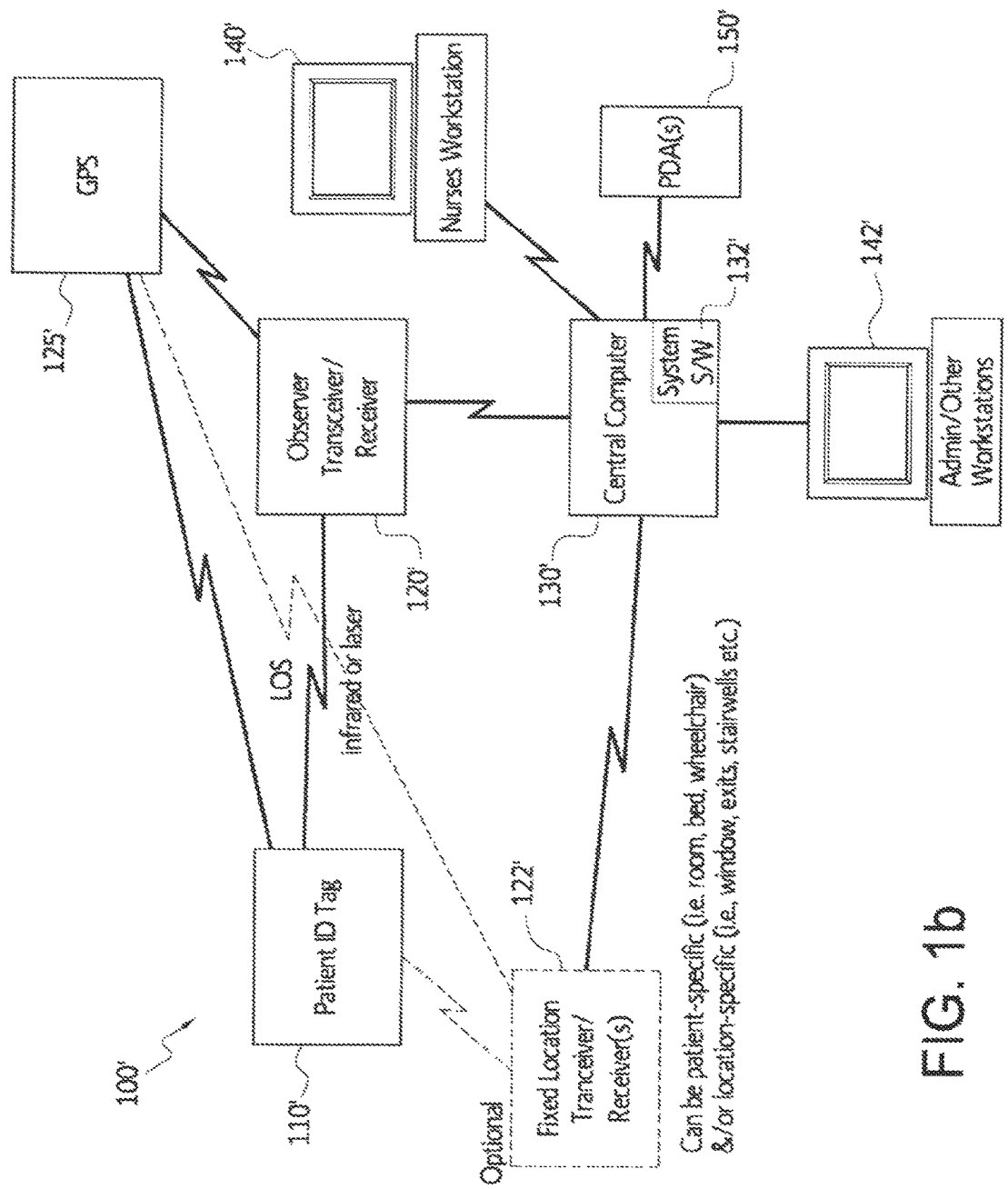
FIG. 1b is a block diagram of an electronic monitoring system using line of sight and infrared and/or laser, in accordance with an embodiment of the disclosed subject matter.

FIG. 1*b* is a block diagram of an electronic monitoring system using line of sight and infrared and/or laser, in accordance with an embodiment of the disclosed subject matter. In FIG. 1*b*, an electronic monitoring system 100' is illustrated that includes a patient identification (ID) tag 110' that is connectible by line-of-sight using infrared and/or laser technology with a generally mobile observer transceiver/receiver (T/R) 120' which serves as a power source and activates the patient identification tag 110' and configured to receive and store GPS satellite positioning information from a GPS system 125'. The electronic monitoring system 100' may optionally include one or more fixed location T/Rs 122' and also serve(s) as a power source to activate the patient identification tag 110'. The T/Rs 120', 122' can also be configured to receive and store GPS satellite positioning information from a GPS system 125' and are further communicatively connected to a central computer system 130' that has an electronic monitoring system software program 132' installed and running. One or more workstations, for example, one or more nurses workstations 140' and/or one or more administrative/administrator or other workstations 142' may be locally and/or remotely connected to the central computer system 130' and the electronic monitoring system software program 132'. In addition, one or more PDA devices 150' may be directly or wirelessly connected to and access the electronic monitoring system software program 132'. The software program 132' will take the transmitted data and convert it to a digital display that shows, for example, the patient identification, observation time, patient activity and the personal identification of the staff member who made the observation. The digital display can be displayed on the observer's handheld device as well as on the workstation and/or PDA tracking screens. If a scheduled observation period is missed, an alarm (visual or by sound, for example) will appear on the screen of the observer T/R 120' and at any workstation and/or PDA, such as a nurse's workstation 140'. The system software 132' will also keep a permanent record of all observation histories that can be downloaded to an archival database on a secure hospital server.

Figure 2:
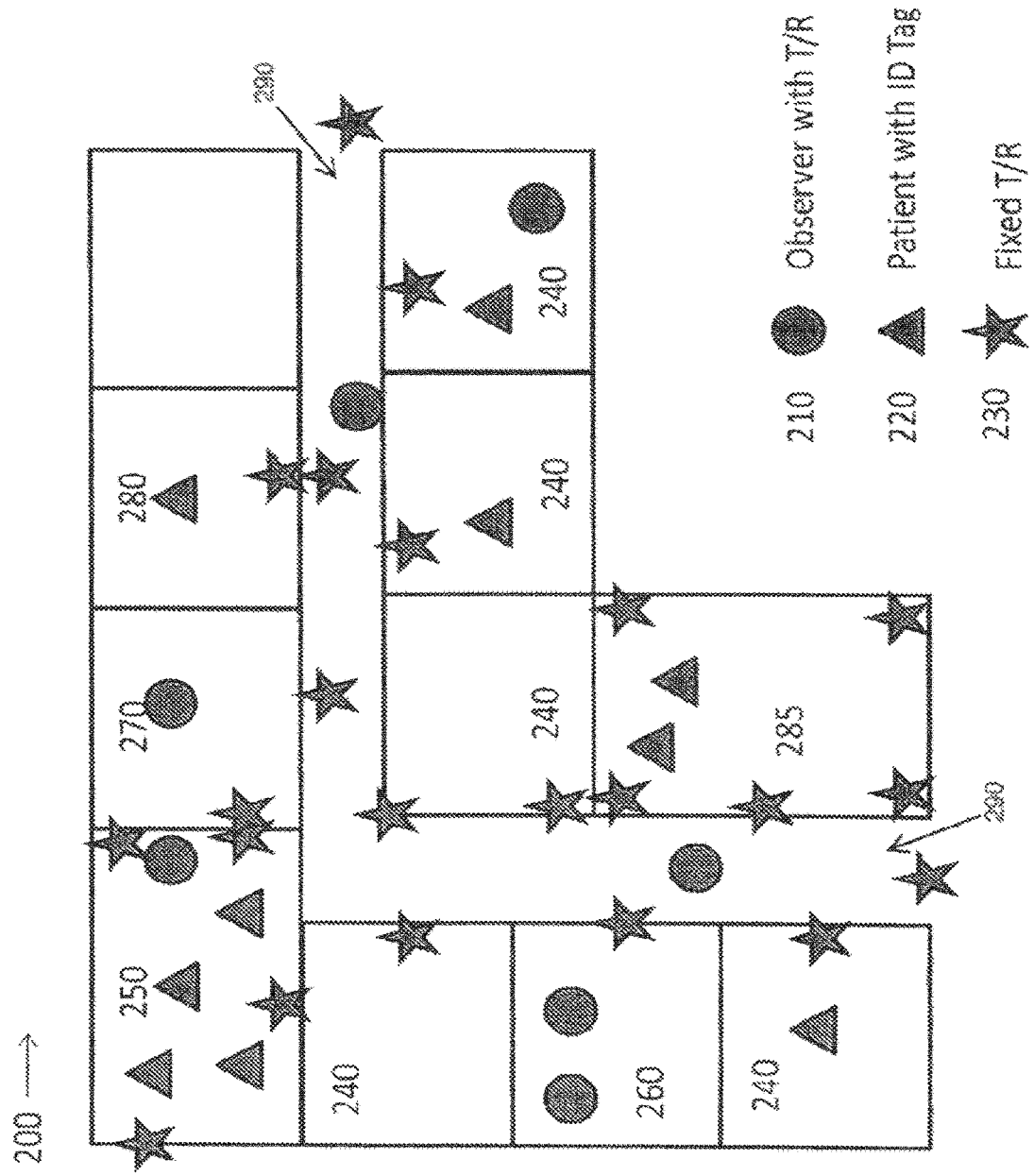
FIG. 2 is a plan view of an exemplary floor plan of a facility in which an electronic monitoring system has been installed, in accordance with one or more embodiments of the disclosed subject matter.

FIG. 2 is a plan view of an exemplary floor plan of a facility in which an electronic monitoring system has been installed, in accordance with one or more embodiments of the disclosed subject matter. In FIG. 2, a floor plan 200 of a facility is shown to include one or more observers with T/R devices 210, one or more patients with ID tags 220, one or more fixed T/R devices 230, multiple patient rooms 240, a dining area 250, at least one nurses station 260, a kitchen area 270, a laundry area 280, a common room 285, and a hallway 290.

Patient information that can be stored on the patient RFID tag 110, 110' includes the patient's hospital identification number, name, diagnosis, risk factors, expected pulse rate and/or other physiological signals to monitor, for example, specified levels of activity or rest. In addition, to the specific patient identification information associated with the tag, the system can monitor the patient's location within the facility and/or in relation to other patients and/or observers.

Using radio waves, the patient's identification tag 110, 110' can be activated and then emit a signal that will be received by a T/R device 120, 120', which is carried or worn by the observer. The frequency of the radio waves can be in compliance with hospital or institution specifications including HIPAA regulations. The observer responsible for visual patient monitoring at set intervals will carry or wear the T/R device 120, 120' that activates the patient RFID tag 110, 110' when the T/R 120, 120' device is within a given distance from the patient RFID tag 110, 110' using, for example, Bluetooth or low-energy Bluetooth devices. This distance or range is adjustable via the adjustments to the transmission signal and may be specified by a responsible treatment team at a particular unit or hospital. The distance is controlled so that it is within a visible range of observer to patient. The patient RFID tag 110, 110' and T/R 120, 120' will permit visual observations, and/or general observations based on distance. The distance between the observer and the patient could range with the capabilities of the RF system. In a typical example, the range would be less than 100 feet but could be as small as one foot. The distance may be set to different values for different observation situations. For example, during sleeping hours, a close observation, say less than 10 feet, may be appropriate, whereas during waking hours, a greater distance, for example, 10 to 25 feet, could be set. The distance can be set under control of the central computer system. Further, the time interval can be changeably set depending on circumstances such as time of day or changing patient needs. The observer T/R device 120, 120' may include any personal digital assistant (such as an iPod, nook, iPhone, iTouch, droid, zigbee, etc) or a wrist display or badge display. For patient tracking, the fixed location T/Rs 122, 122' operate in the same manner as the observer T/Rs with the exception that it is the patient's movement to within a given, predefined distance from the fixed location T/Rs 122, 122' that causes the fixed location T/Rs 122, 122' to activate the patient RFID tag 110, 110'.

Figure 3A:
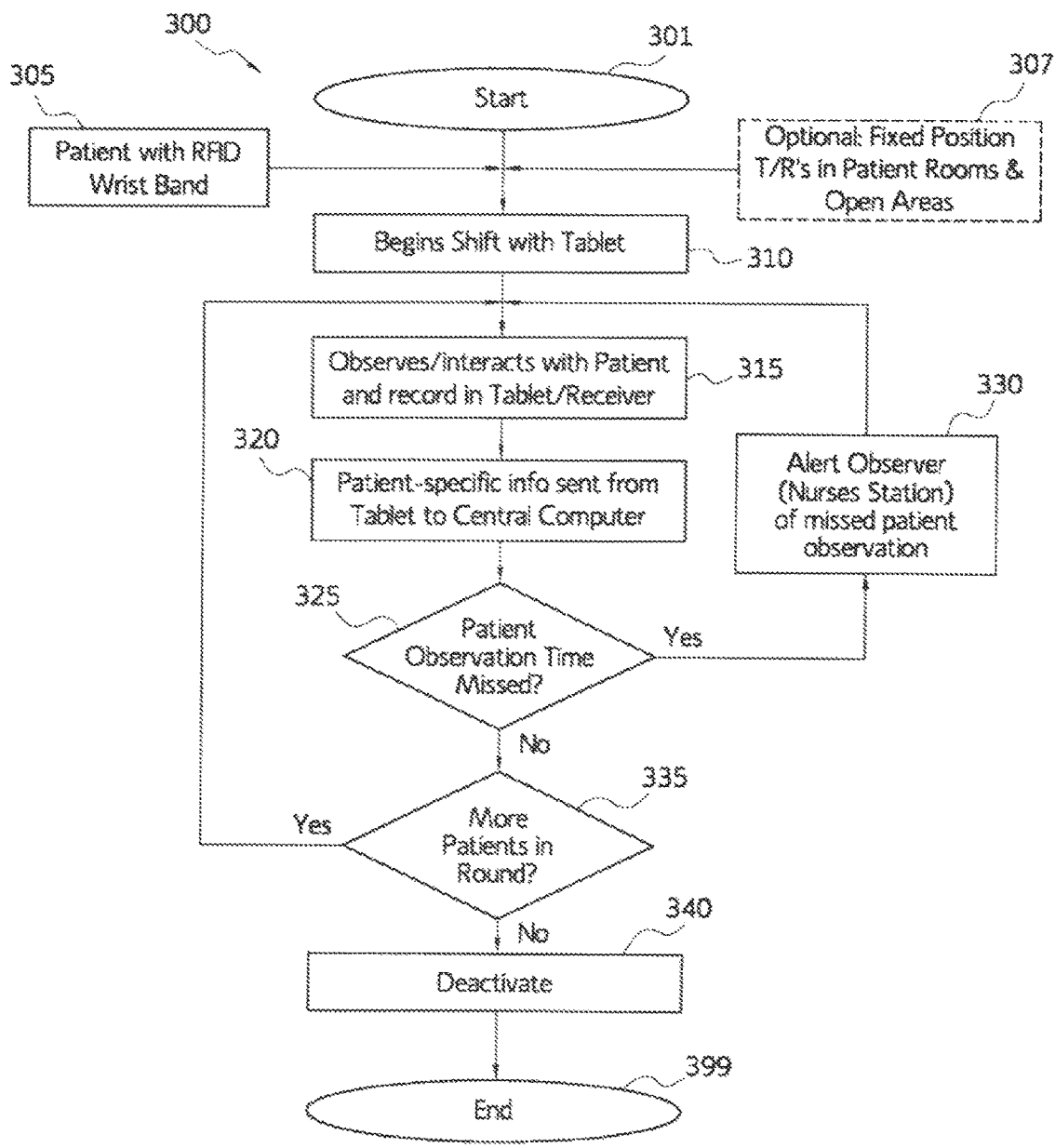
FIG. 3a is a flow chart illustrating the process followed by an observer using an electronic patient monitoring system, in accordance with an embodiment of the disclosed subject matter.

FIG. 3*a* is a flow chart illustrating the process followed by an observer using an electronic patient monitoring system, in accordance with an embodiment of the disclosed subject matter. In FIG. 3*a*, the process is started 301 with an observer beginning their work shift and activating 310 a T/R with pre-assigned patient ID numbers and round/visual observation schedule. Prior to these steps, all patients being monitored by the system are equipped 305 with an ID tag that contains information specific to each patient and, optionally, fixed position T/Rs can be affixed 307 to walls and/or other parts of the facility in various locations in the facility. As the observer observes/interacts 315 with the patients, the information from each patient's ID tag as well as the time of the interaction and other patient-specific information are automatically recorded. After a predefined time period, for example, immediately, every minute, etc., all information recorded by the T/R is sent 320 to the central computer to be processed and stored. For example, the electronic patient monitoring system, which can be implemented in a software program, will take the transmitted data and convert it to a digital display that shows, for example, the patient identification, observation time, patient activity and the personal identification of the staff member who made the observation. The digital display can be displayed on the observer's handheld device as well as on the workstation tracking screen. If a scheduled visual observation check is missed within the given time interval, an alarm (visual or by sound, for example) will appear on the screen of the observer and at any workstation, such as a nurse's station. The software will also keep a permanent record of all observation histories that can be downloaded to an archival database on a secure hospital server. If a missed patient visual observation check is detected 325, an alert is sent 330 to the observer, the nurse's station, other observers, etc. and the observer is directed to locate and observe/interact 315 with the missed patient. If the patient visual observation check was detected 325, then the observer determines 335 whether there are additional patients to be observed. If there are more patients to be observed, the observer is directed to locate and observe/interact 315 with the next patient. If there are no more patients to be observed, the observer is directed to deactivate 340 the T/R and the observation process ends 399.

The RFID tag and T/R devices may be utilized at fixed locations within the unit or facility to monitor patient location, and permit notification via warning light or alarm when patients or staff members are near or have entered areas which have restrictions to access. The RFID tag and observer's T/R device will also function mobily, which is not dependent on a fixed location of service. Once the RFID tag is activated, a signal is sent to the activating fixed location or observer T/R device. The T/R device registers the patient information from the RFID tag in software included in the observer T/R device. This includes an electronic checklist that ensures and documents the signal was received in the given time requirement imposed by the treatment team or facility guidelines.

Software in the T/R device, and at the central nurses' station, gives a warning signal (such as a yellow light or beep), if a patient has not been successfully visually observed within the given time interval specified by the patient's treatment team. This system presents the observer with immediate feedback to go and check on the missed patient. The time interval may be scheduled as continuous (i.e., real time) monitoring, a predetermined number of minutes (e.g., every 1, 5, 10, 15 or 30 minutes, or increments thereof), hourly monitoring or rounding, monitoring for a predetermined number of hours, or daily monitoring. After the patient has been identified, a note is made in the software and the process is reset to continue with normal monitoring. In addition to the patient-specific feedback, the system can also provide statistical compliance feedback to each observer of one or measures of the individual observer's performance. In general, this feedback can be provided to each observer in real time, so the observers know exactly how they are performing at any given point in time, or at least with only a minimal delay, for example, but not limited to, a few seconds. This can be used as a way to motivate each observer to, if necessary, self-correct to maintain their level of performance at or above the necessary levels needed for compliance with the required observation schedules.

In addition to receiving and storing the patient information after the visual observation has been made in the given distance from the patient, the observer T/R device automatically transmits the data wirelessly to a centralized software system. The data can also be incorporated into a more comprehensive electronic medical record.

Centralized Software Monitoring and Warning System. The T/R sends the visual observation patient data to a centralized software system wirelessly and in real time. The software stores the patient identification documentation as collected by the T/R device. Additionally, the centralized software signals an alert (e.g., by light or sound) when a patient observation is missed during a prescribed time interval and generates reports of documented observations.

The centralized software generates an alert of a missed patient observation to, for example, but not limited to, immediately activate any identified camera systems within the assigned proximity of the unit or identified geographical region, activate an emergency response system which may include automatically locking doors permitting outside access, activation of an overhead public announcement system to provide information and alarms, and a visual representation of the location of all identified patients on the unit.

The centralized software can be accessed from a nurses' station in the psychiatric unit, where the nurses' station attendants would also be alerted to any missed visual observation checks. This component to the system adds a secondary check to the observation system in addition to the primary observer responsible for the visual checks. Now, a second nurse or attendant at the nursing station could also be alerted in real time that a patient observation has been missed.

The centralized software can create an alert (by light or sound) when a patient demonstrates a heightened pulse interval, as predetermined based on clinical criteria.

Figure 3B:
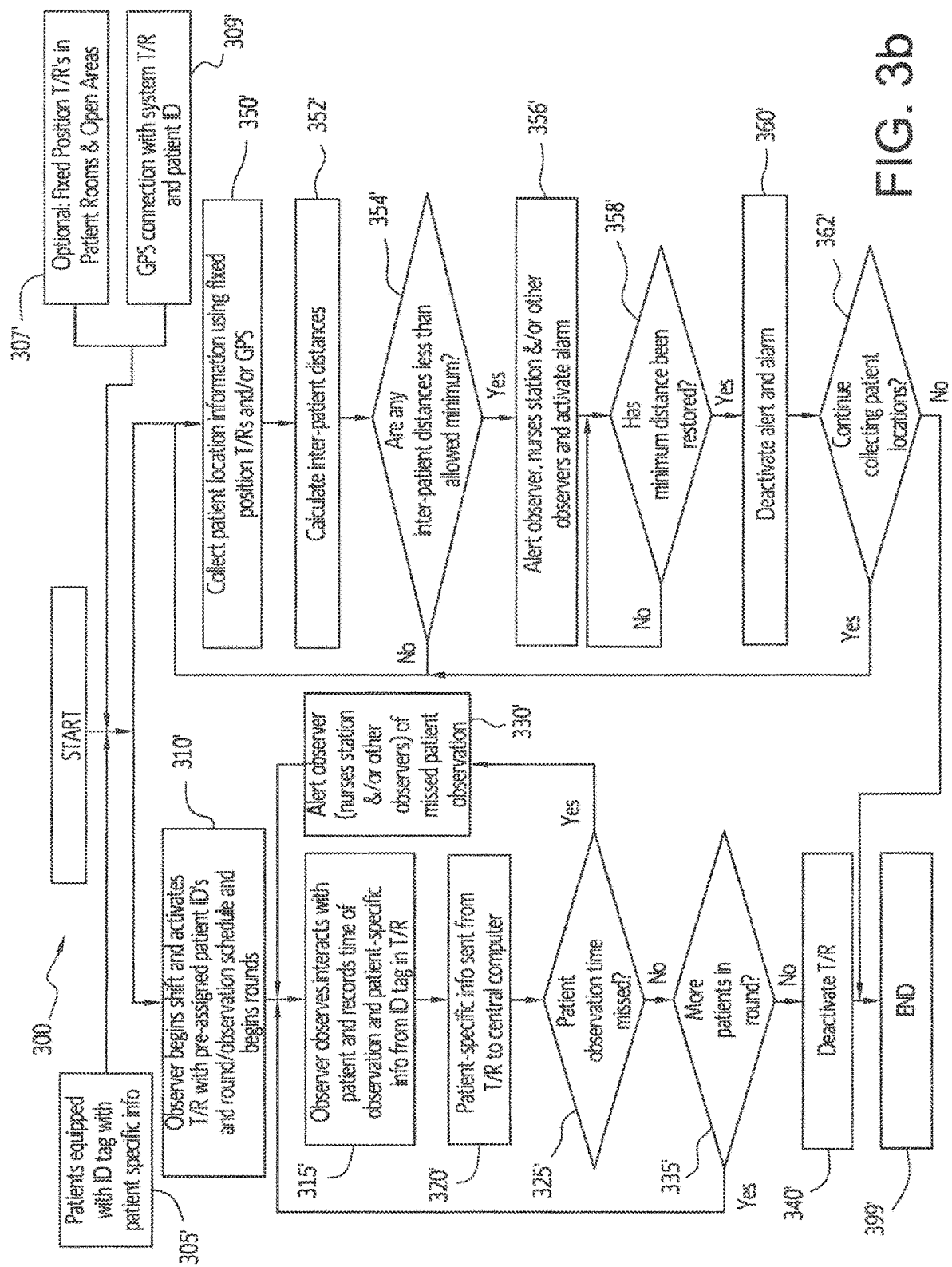
FIG. 3b is a flow chart illustrating the process followed by an observer using an electronic patient monitoring system with GPS and inter-patient distance monitoring, in accordance with an embodiment of the disclosed subject matter.

FIG. 3b is a flow chart illustrating the process followed by an observer using an electronic patient monitoring system, in accordance with an embodiment of the disclosed subject matter. In FIG. 3b, the process is started 301' with an observer beginning their work shift and activating 310' a T/R with pre-assigned patient ID numbers and round/visual observation schedule. Prior to these steps, all patients being monitored by the system are equipped 305' with an ID tag that contains information specific to each patient and, optionally, fixed position T/Rs can be affixed 307' to walls and/or other parts of the facility in various locations in the facility. The system (i.e., the central computer, T/Rs, and patient ID tags) can also be connected 309' to and use GPS position information. Alternatively, the system can use Bluetooth or low-energy Bluetooth proximity and patient information that is exchanged between the patient ID tag and the observer T/R. As the observer observes/interacts 315' with the patients, the information from each patient's ID tag as well as the time of the interaction and other patient-specific information are automatically recorded. After a predefined time period, for example, immediately, every minute, etc., all information recorded by the T/R is sent 320' to the central computer to be processed and stored. For example, the electronic patient monitoring system, which can be implemented in a software program, will take the transmitted data and convert it to a digital display that shows, for example, the patient identification, observation time, patient activity and the personal identification of the staff member who made the observation. The digital display can be displayed on the observer's handheld device as well as on the workstation tracking screen. If a scheduled observation period is missed, an alarm (visual or by sound, for example) will appear on the screen of the observer and at any workstation, such as a nurse's station. The software will also keep a permanent record of all observation histories that can be downloaded to an archival database on a secure hospital server. If a missed patient observation time is detected 325', an alert is sent 330' to the observer, the nurse's station, other observers, etc. and the observer is directed to locate and observe/interact 315' with the missed patient. If a missed patient observation time was not detected 325', then the observer determines 335' whether there are additional patients to be observed. If there are more patients to be observed, the observer is directed to locate and observe/interact 315' with the next patient. If there are no more patients to be observed, the observer is directed to deactivate 340 the T/R and the observation process ends 399'.

In FIG. 3b, concurrently with and independently from the observer observation process described above, the system can collect patient location information within the facility and determine inter-patient distances to ensure minimum safe patient-to-patient distances are maintained. After the process is started 301', the system begins to collect 350' patient location information using the GPS or other positioning/tracking system, Bluetooth, low-energy Bluetooth proximity information, and/or fixed-position T/Rs. Once collected, the system calculates 352' the inter-patient distances, which can include distances between a patient and every other patient, a patient and only selected other patients, distances between multiple (i.e., 3 or more) patients. This information can also be used to calculate a patient's or group of patients' position relative to restricted areas. After the inter-patient distances are calculated 352', the system determines 354' whether any of the distances are less than a pre-defined minimum distance and, if not, the system returns to and continues to collect 350' patient location information. If so, the system alerts 356' the patient's observer(s), the nurse's station and/or other observers and activates an alarm. The system then determines 358' whether the minimum distance has been restored and, if not, continues to determine 358' whether the minimum distance has been restored. If the minimum distance is determined 358' to have been restored, then the system deactivates the alarm 360' and determines 362' whether to continue to collect patient locations and, if so, returns to and continues to collect 350' patient location information. If not, the patient location collection process ends 399'.

Figure 4:
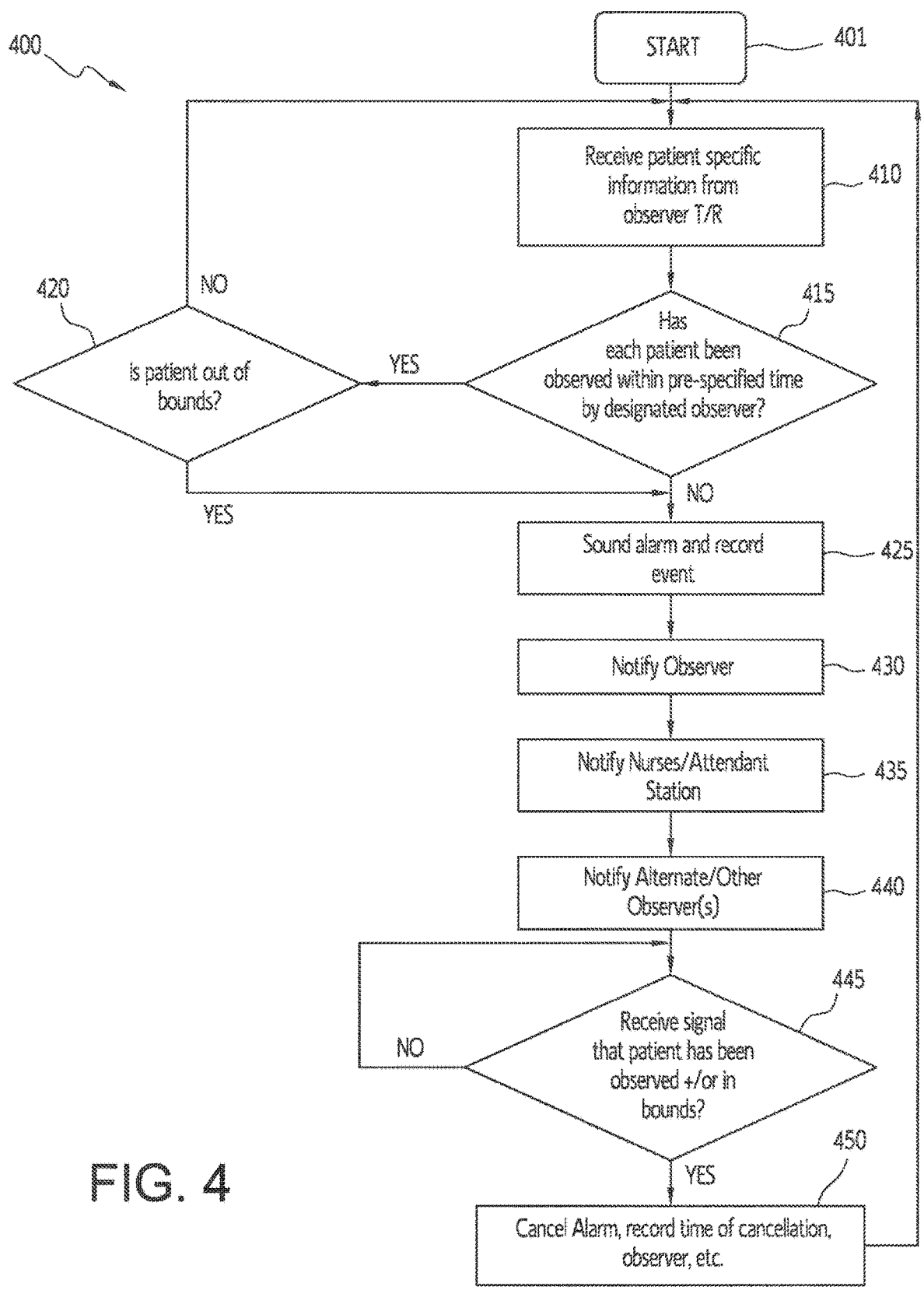
FIG. 4 is a flow chart illustrating the functional operation of an electronic monitoring system, in accordance with an embodiment of the disclosed subject matter.

FIG. 4 is a flow chart illustrating the functional operation of an electronic monitoring system, in accordance with an embodiment of the disclosed subject matter. In FIG. 4, a flow chart 400 illustrating the functional operation of an electronic monitoring system software program is shown. Following start up 401 the program begins receiving 410 patient-specific information from one or more observer T/R devices. This information is used by the program to determine 415 whether all patients have been observed within the pre-specified time interval for each patient. If it is determined 415 that the patient was timely observed, the program determines based on the received patient information whether the patient is "out of bounds," i.e., not in their approved area of movement, which may vary based on the time of day, and if out of bounds, or if it was determined 415 that the patient was not timely observed, the program sounds 425 an alarm and records the event. If the patient was determined 420 to be "in bounds," i.e., in their approved area of movement and/or a required distance away from other patients and/or areas, the system returns to receiving 410 patient information. After an alarm is sounded 425, the observer responsible for the patient is notified 430, a nurse's/attendant station is notified 435 and alternate/other observers are also notified 440 of the missed patient observation. On the observer T/R device and nursing workstation (or other workstation) there would be an override which could only be accessed via a password by approved override staff member. The staff member could also code in the reason for override (for example, from a drop down menu). Once a signal has been received 445 to indicate that the patient has either been observed and/or is now in bounds, the alarm is cancelled 450 and associated information with the cancellation (e.g., time of cancellation, ID of the observer that observed the patient, etc.) is recorded, the system returns to receiving 410 regularly scheduled patient observation information.

Further, administrators could also monitor in real time observer compliance to help assess observer quality and to assess perturbations in the process which make it more likely to miss a visual observation, such as a psychiatric counseling session or a medical test. This would allow the ability to fine-tune the observation system to better ensure that a patient is monitored at all prescribed time intervals and to better prevent an adverse event (suicide or self-harming attempt) from occurring.

Hourly Rounding. Hourly rounding will be measured and documented by a RFID tag and T/R device in the same manner as previously described. If transmission is not made during the predetermined time interval a light and/or audible alarm will be sounded by the centralized software area at the nurses' station. Based upon a predetermined line of sight proximity an interaction time measurement will be monitored between caregiver and patient to determine the interaction time between the participants for each hourly rounding event.

The centralized software station will document the timeliness of each caregiver as they complete their hourly rounds, as well as the interaction time spent with the patient within a predetermined line of sight proximity. Interaction time indirectly provides information to better assist quality indicators of interaction directly relating to patient care and satisfaction.

Figure 5:
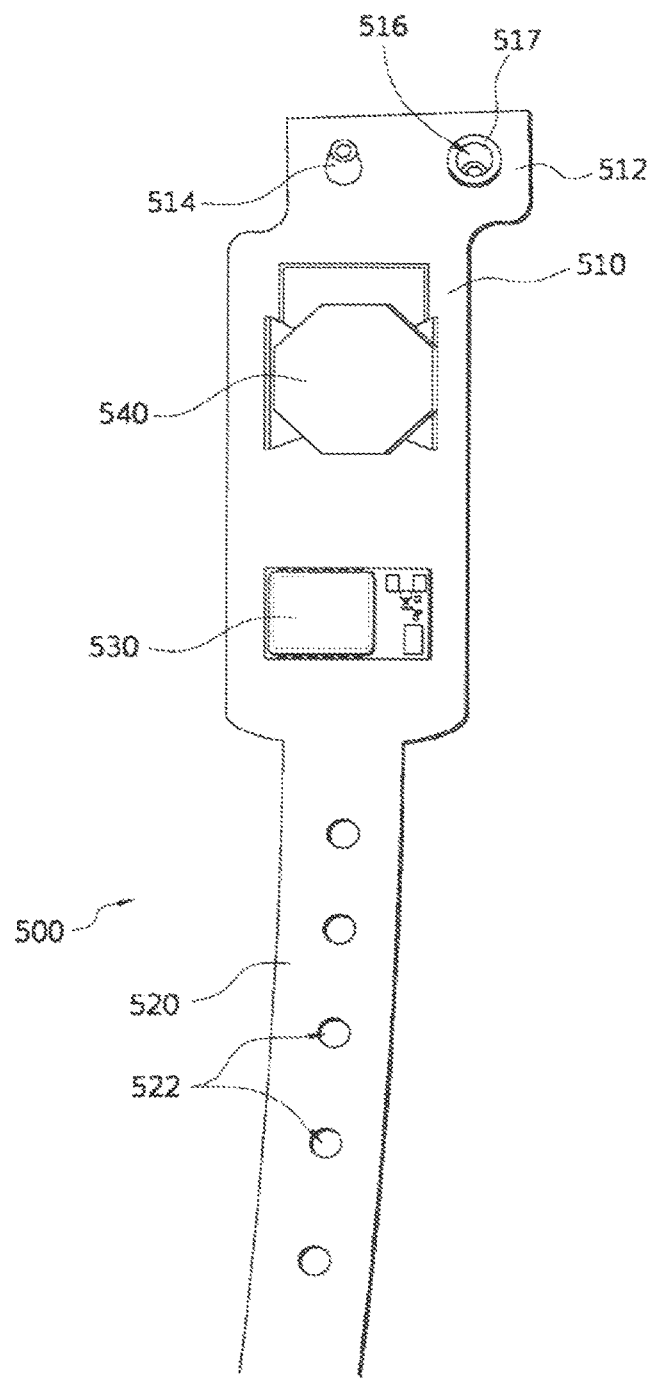
FIG. 5 is a top view of a patient identification tag that uses radio frequency (such as Bluetooth or low energy Bluetooth technology), in accordance with an embodiment of the disclosed subject matter.

Prevention of harm/inappropriate behavior. A measurement of patient-to-patient proximity can be obtained by for example, GPS coordinates or an active transmitter on each patient, for example, a Bluetooth or low-energy Bluetooth device, that will signal when a given distance would be achieved to ensure that an appropriate distance between patients is maintained. Based on a predetermined acceptable distance of identified patients, hour of the day, or unit location patients determined to be at risk will trigger notification of the central software system via green, yellow or red light or audible alarm when identified patients are within a predetermined proximity as measured by RFID tag transmission FIG. 5 is a top view of a patient identification tag that uses low energy Bluetooth technology, in accordance with an embodiment of the disclosed subject matter. In FIG. 5, a patient identification tag 500 includes a body portion 510 that is attached to a strap portion 520, which has multiple openings 522 defined in the strap portion 520. The body portion 510 includes a Bluetooth low energy (BLE) RFID beacon device 530 that can transmit a signal having a 360° range of about 10 to 20 feet from the device. A battery holder 540 is also attached to the body portion 510 and is configured to receive and hold a flat battery (not shown) and is electrically connected to a BLE RFID beacon device 530. The body portion 510 also includes a top flange 512 on which are located a pin 514 that is positioned and configured to fit within the openings 522 on the strap portion 520. An opening 516 is formed in the top flange 512 adjacent the pin 514 and has a grommet 517 securely fastened within the opening 516 and the grommet 517 is configured to fit onto and securely hold the pin 514 after the identification tag 500 has been placed around a patient's wrist and one of the opening 522 on the strap portion 520 have been fitted over the pin 514.

Figure 6:
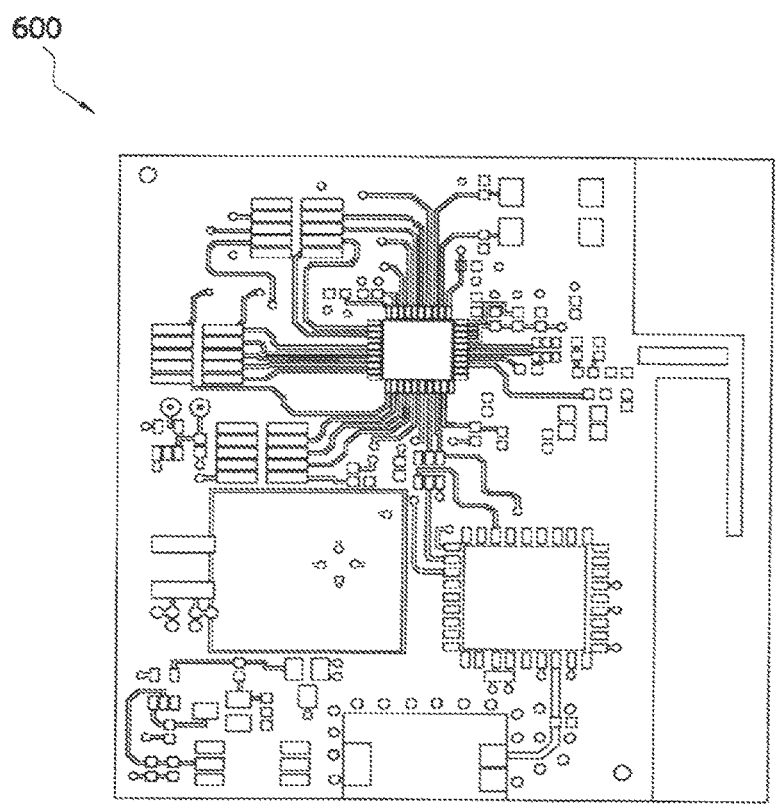
FIG. 6 is a top view of an example of a radio frequency (such as Bluetooth or low energy Bluetooth technology) circuit board which can be used for a patient identification tag, in accordance with an embodiment of the disclosed subject matter.

FIG. 6 is a top view of a flexible Bluetooth low energy circuit board for use in a patient identification tag, in accordance with an embodiment of the disclosed subject matter. In FIG. 6, an example of a flexible active circuit board 600 that includes the transmission components and patient identification data is illustrated.

Figure 7B:
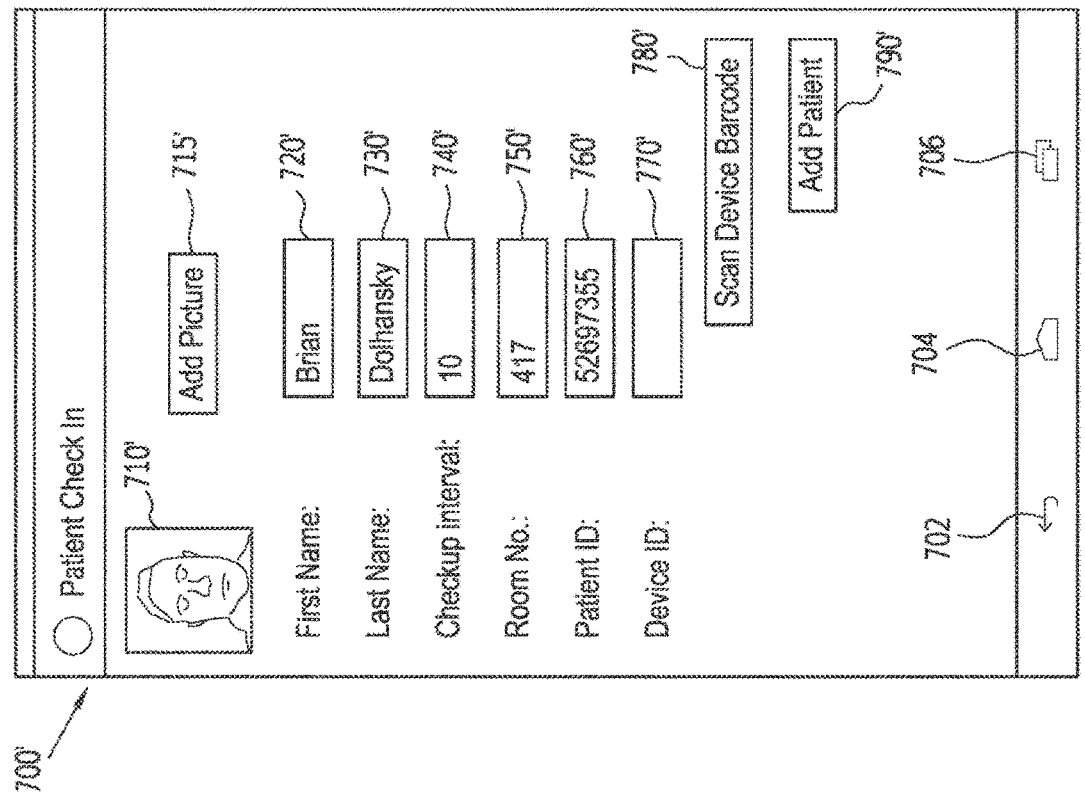
FIG. 7b is a view of a patient check-in screen in an electronic monitoring system, in accordance with an embodiment of the disclosed subject matter.
Figure 7A:
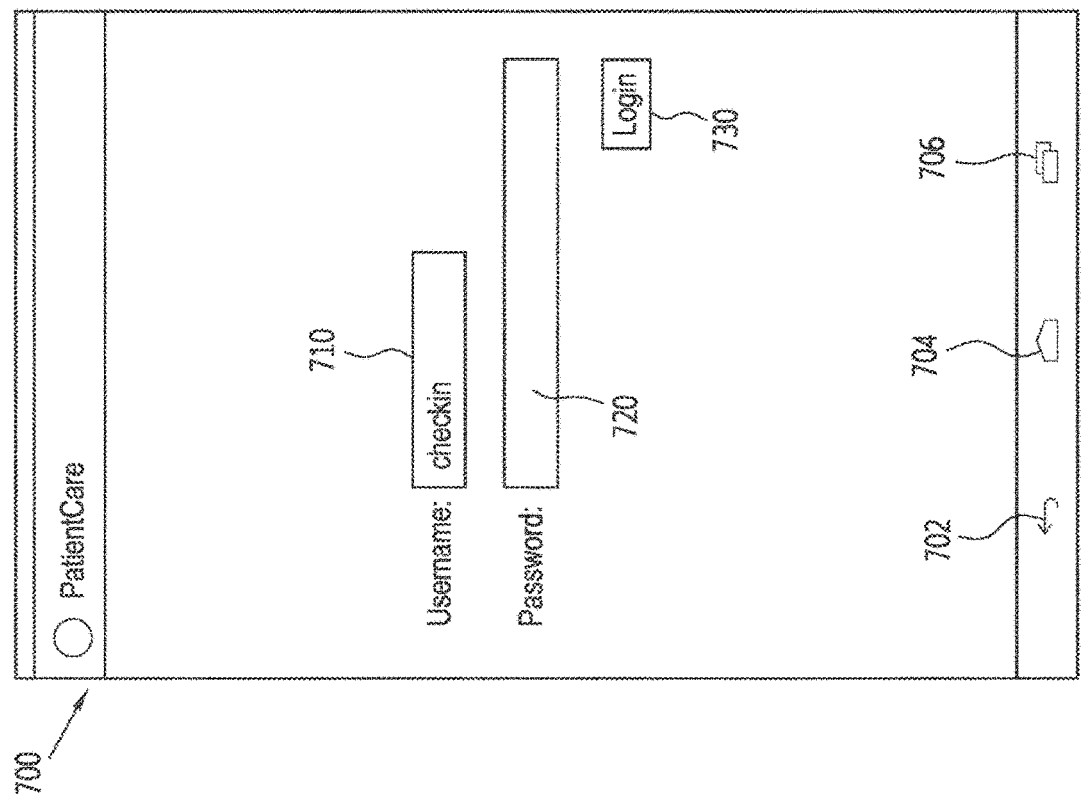
FIG. 7a is a view of a check-in login screen for an electronic monitoring system, in accordance with an embodiment of the disclosed subject matter.

FIG. 7*a* is a view of a check-in login screen for a user device in an electronic monitoring system, in accordance with an embodiment of the disclosed subject matter. In FIG. 7*a*, a screen 700 is displaying a login screen that includes a username entry box 710 and password entry box 720, a login selection button 730, a return icon 702, a movement icon 704 and a page change icon 706. The username entry box 710 is configured to receive a check-in user name and the password entry box 720 is configured to receive a check-in password associated with the check-in user name and the login selection button 730 is configured to be selected after the user name and password have been entered and to pass control to the program to determine whether the correct user name and password combination were entered and to determine what information and user rights are associated with the user name and password and them display that information on the screen, for example, as shown in FIG. 7*b*. When selected, the return icon 702 displays the prior screen information, the movement icon 704 permits a user to scroll up and down depending on the amount of information on each page and the current position in the information on the page, and, if more than one page of patient information is associated with the patient, the page change icon 706 permits a user to move forward and backward through the pages.

FIG. 7*b* is a view of a patient check-in screen in an electronic monitoring system, in accordance with an embodiment of the disclosed subject matter. In FIG. 7*b*, a patient check-in screen 700' is shown to include a picture of a patient 710', an add picture button 715', a first name input box 720', a last name input box 730', a check-up interval input box 740', a room number input box 750', a patient ID input box 760', a device ID input box 770', a scan device barcode selection button 780', an add patient selection button 790', the return icon 702, the movement icon 704 and the page change icon 706. When the add picture button 715' is selected a picture of the patient may be added by, for example, but not limited to, taking a picture with a camera that is part of, connected to or associated with the user device, downloading the picture from a storage device that is connected to the user device, etc. When the scan device barcode selection button 780' is manually selected, the user device will scan the barcode associated with the patient's identification tag. Alternatively, in embodiments of the disclosed subject matter that use the BLE RFID tags, selecting the scan device barcode selection button 780' would cause the user device to read the RFID device number associated with the patient's ID tag. Still further, the user device could automatically detect a signal from and read the RFID device number associated with the patient's ID tag when the user device comes within the transmit range of the RFID device.

Figure 8B:
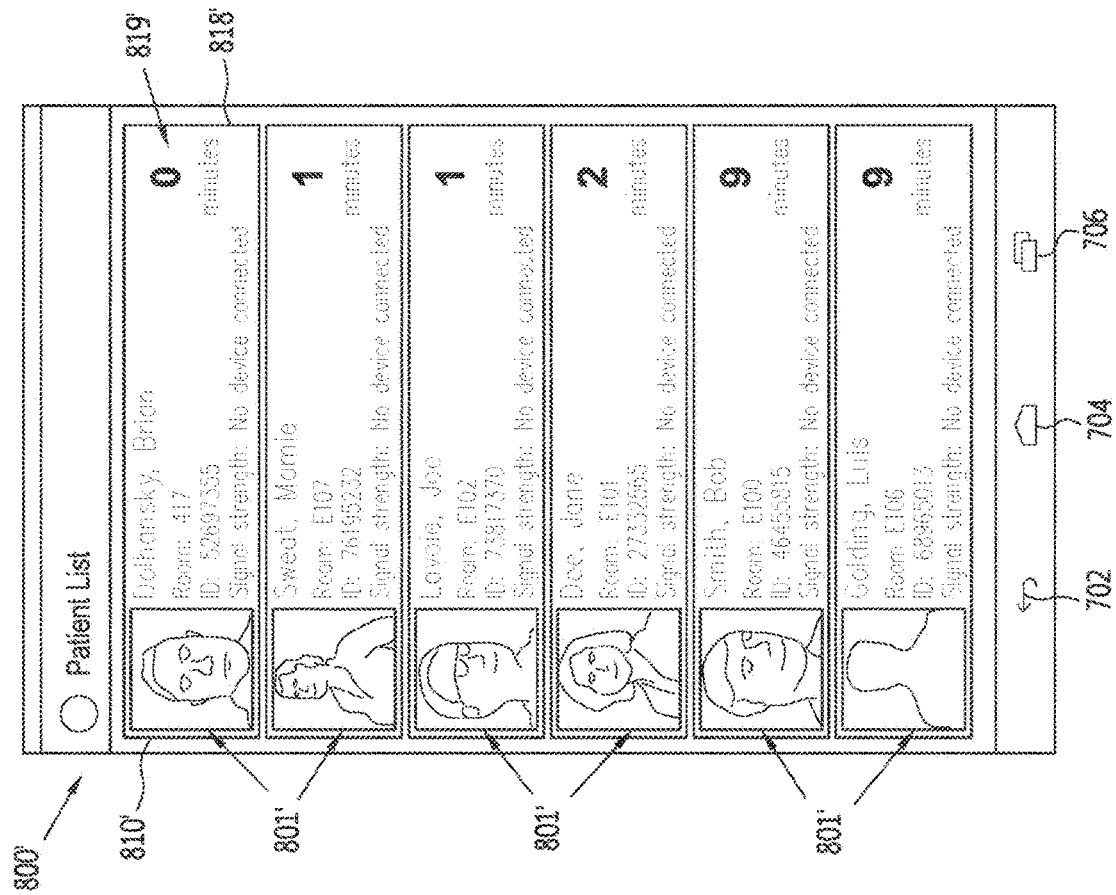
FIG. 8b is a view of a patient list screen in an electronic monitoring system, in accordance with an embodiment of the disclosed subject matter.
Figure 8A:
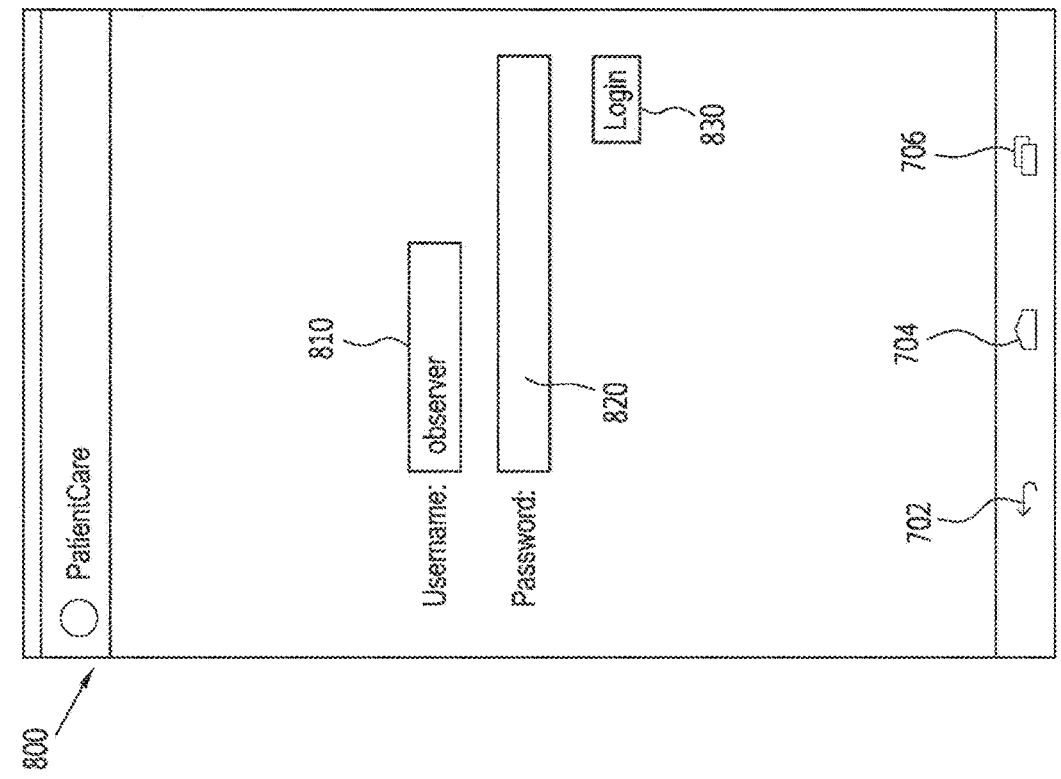
FIG. 8a is a view of an observer login screen for an electronic monitoring system, in accordance with an embodiment of the disclosed subject matter.

FIG. 8*a* is a view of an observer login screen for a user device in an electronic monitoring system, in accordance with an embodiment of the disclosed subject matter. In FIG. 8*a*, a screen 800 is displaying a login screen that includes an observer's username entry box 810 and password entry box 820, a login selection button 830, a return icon 802, a movement icon 804 and a page change icon 806. The username entry box 810 is configured to receive an observer's user name and the password entry box 820 is configured to receive an observer password associated with the observer's user name and the login selection button 830 is configured to be selected after the observer's user name and password have been entered and to pass control to the program to determine whether the correct observer's user name and password combination were entered and to determine what information and user rights are associated with the observer's user name and password and them display that information on the screen, for example, as shown in FIG. 8*b*. When selected, the return icon 802 displays the prior screen information, the movement icon 804 permits a user to scroll up and down depending on the amount of information on each page and the current position in the information on the page, and, if more than one page of patient information is associated with the patient, the page change icon 806 permits a user to move forward and backward through the pages.

FIG. 8*b* is a view of a patient list screen in an electronic monitoring system, in accordance with an embodiment of the disclosed subject matter. In FIG. 8*b*, a patient list screen 800' is shown to include multiple patient information summaries 801' that each display a picture or generic silhouette of a patient 810', a last and first name of the patient 812', a room number 814', a last name input box 816', a signal strength indication 818', a time remaining to observe 819', the return icon 702, the movement icon 704 and the page change icon 706. When the observer comes within range of each patient's RFID tag, the device automatically detects the signal and reads the RFID device number associated with the patient's ID tag as well as any other pertinent patient data, for example, vital statistics, actual location, activity, etc. As seen in FIG. 8*b*, a first patient information summary 801' for "Dolhansky, Brian" is highlighted to indicate that the required observation time has passed (note the 0 minutes value displayed for the time remaining to observe 819') and that no actual observation of the patient has been recorded.

Figures 9A, 9B:
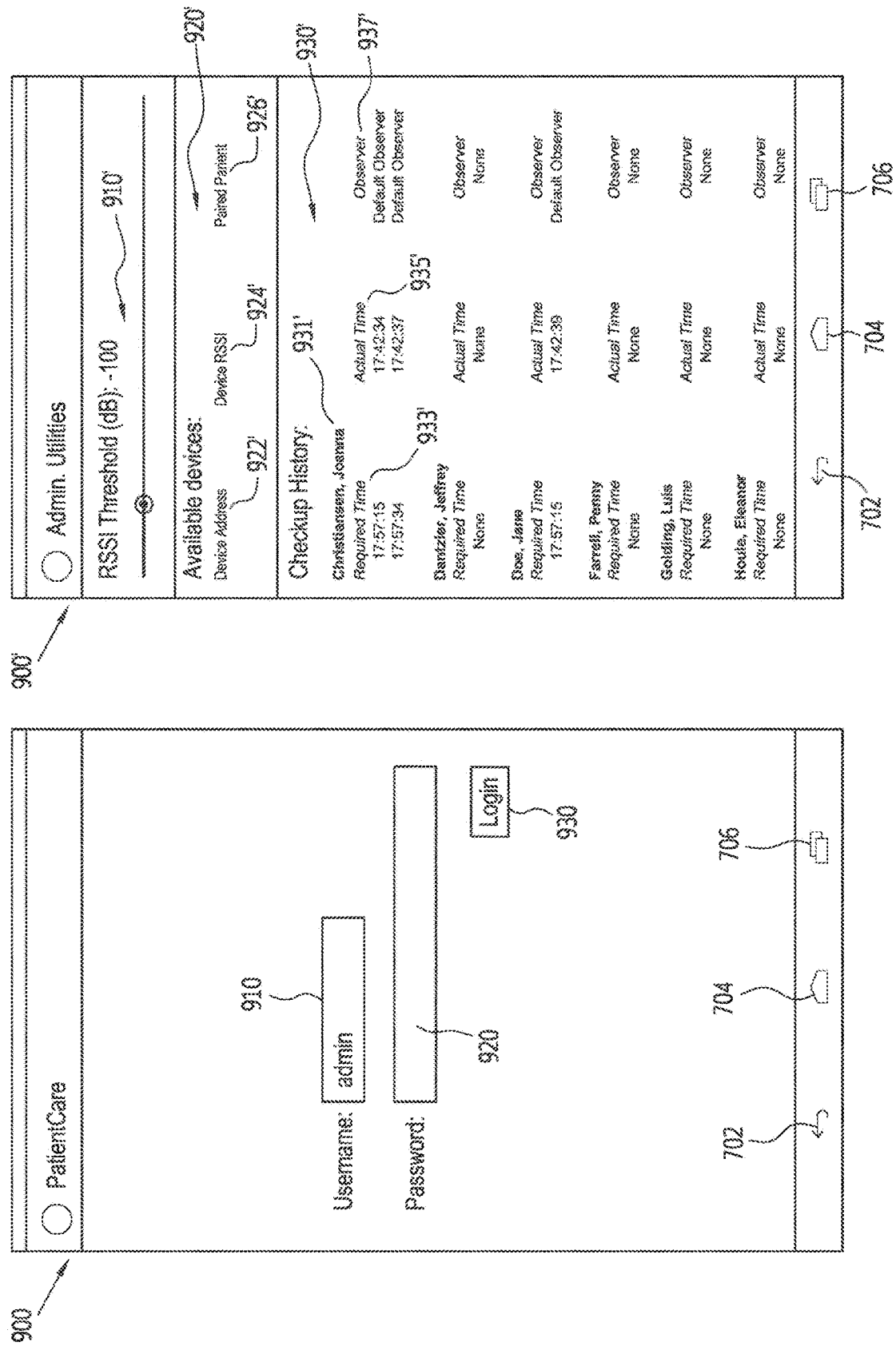
FIG. 9a is a view of an administrator login screen for an electronic monitoring system, in accordance with an embodiment of the disclosed subject matter.
FIG. 9b is a view of a patient checkup history screen in an electronic monitoring system, in accordance with an embodiment of the disclosed subject matter.

FIG. 9*a* is a view of an administrator login screen for a user device in an electronic monitoring system, in accordance with an embodiment of the disclosed subject matter. In FIG. 9*a*, a screen 900 is displaying a login screen that includes an administrator's username entry box 910 and password entry box 920, a login selection button 930, a return icon 902, a movement icon 904 and a page change icon 906. The username entry box 910 is configured to receive an administrator's user name and the password entry box 920 is configured to receive an administrator password associated with the administrator's user name and the login selection button 930 is configured to be selected after the administrator's user name and password have been entered and to pass control to the program to determine whether the correct administrator's user name and password combination were entered and to determine what information and user rights are associated with the administrator's user name and password and them display that information on the screen, for example, as shown in FIG. 9*b*. When selected, the return icon 902 displays the prior screen information, the movement icon 904 permits a user to scroll up and down depending on the amount of information on each page and the current position in the information on the page, and, if more than one page of patient information is associated with the patient, the page change icon 906 permits a user to move forward and backward through the pages.

FIG. 9*b* is a view of a patient checkup history screen in an electronic monitoring system, in accordance with an embodiment of the disclosed subject matter. In FIG. 9b, an administrative utilities screen 900' is shown to include a received signal strength indication (RSSI) Threshold value 910', a listing of available devices section 920' with information for each device including a device address 922', a device RSSI 924' and a paired patient name 926', and a patient checkup history section 930' with separate information for each patient that includes a required patient observation time 933', an actual patient observation time 935' and an assigned observer name for the patient 937'.

Figure 10:
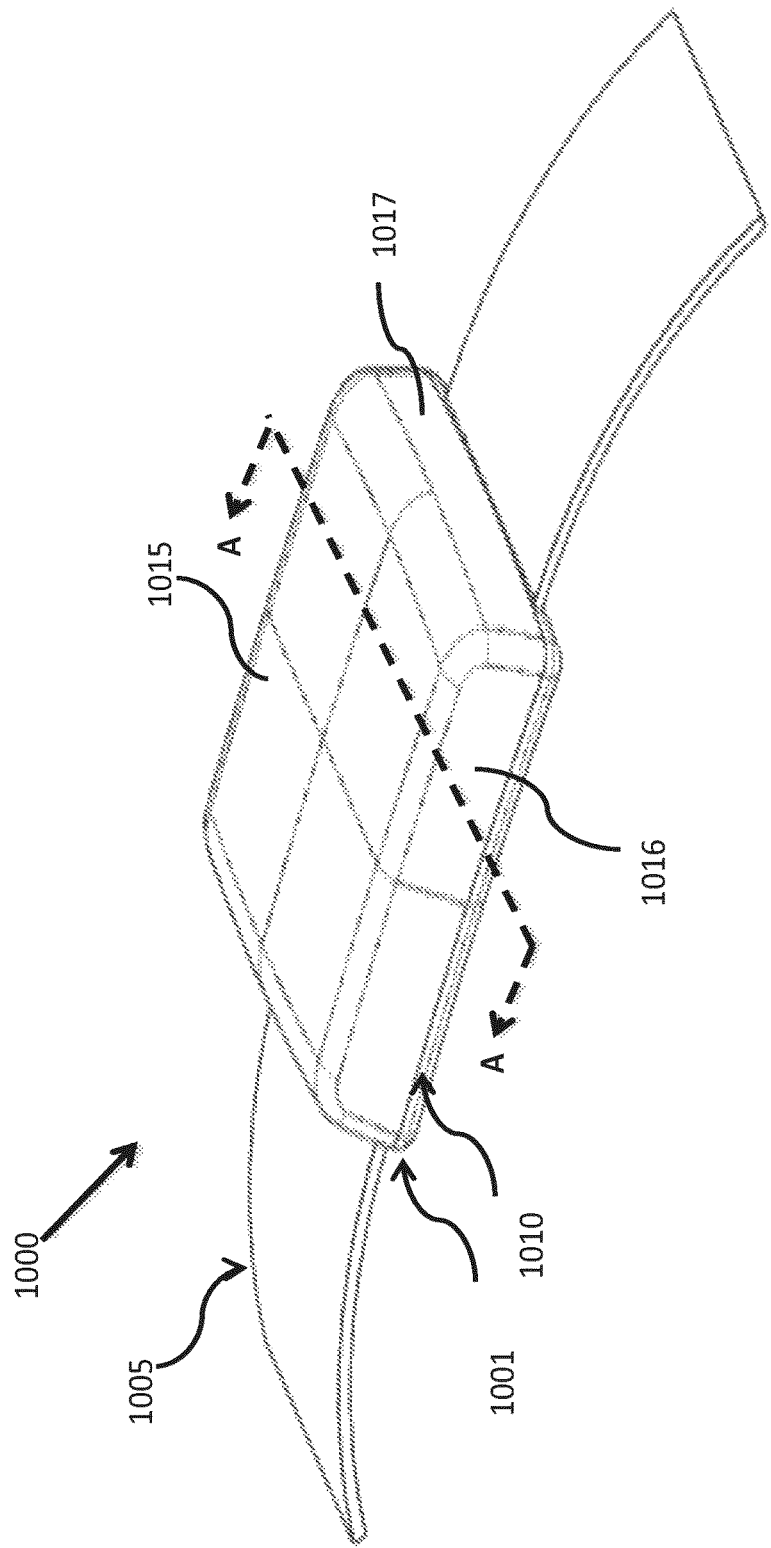
FIG. 10 is a top perspective view of a clasp and partial portion of a wristband, in accordance with an embodiment of the disclosed subject matter.

FIG. 10 is a top perspective view of a clasp and partial portion of a wristband, in accordance with an embodiment of the disclosed subject matter. In FIG. 10, a wristband and clasp system 1000 includes a tamper-resistant wristband band material 1005 and an assembled clasp 1001 that holds two ends of the wristband 1005 together securely on a person's wrist, for example, but not limited to, the wristband 1005 can be a woven band ¾ inch wide by 0.040 inch thick, which has a plurality of openings 1006 formed there through and adjacent to each end 1008 of the wristband 1005. The clasp includes four parts: a top portion 1010, a bottom portion 1020 (see FIG. 11) and two non-retractable spring slides 1022 (see FIG. 11), which can be pre-assembled and retained in opposite longitudinal grooves 1024 in the body of the bottom portion 1020.

Figure 11:
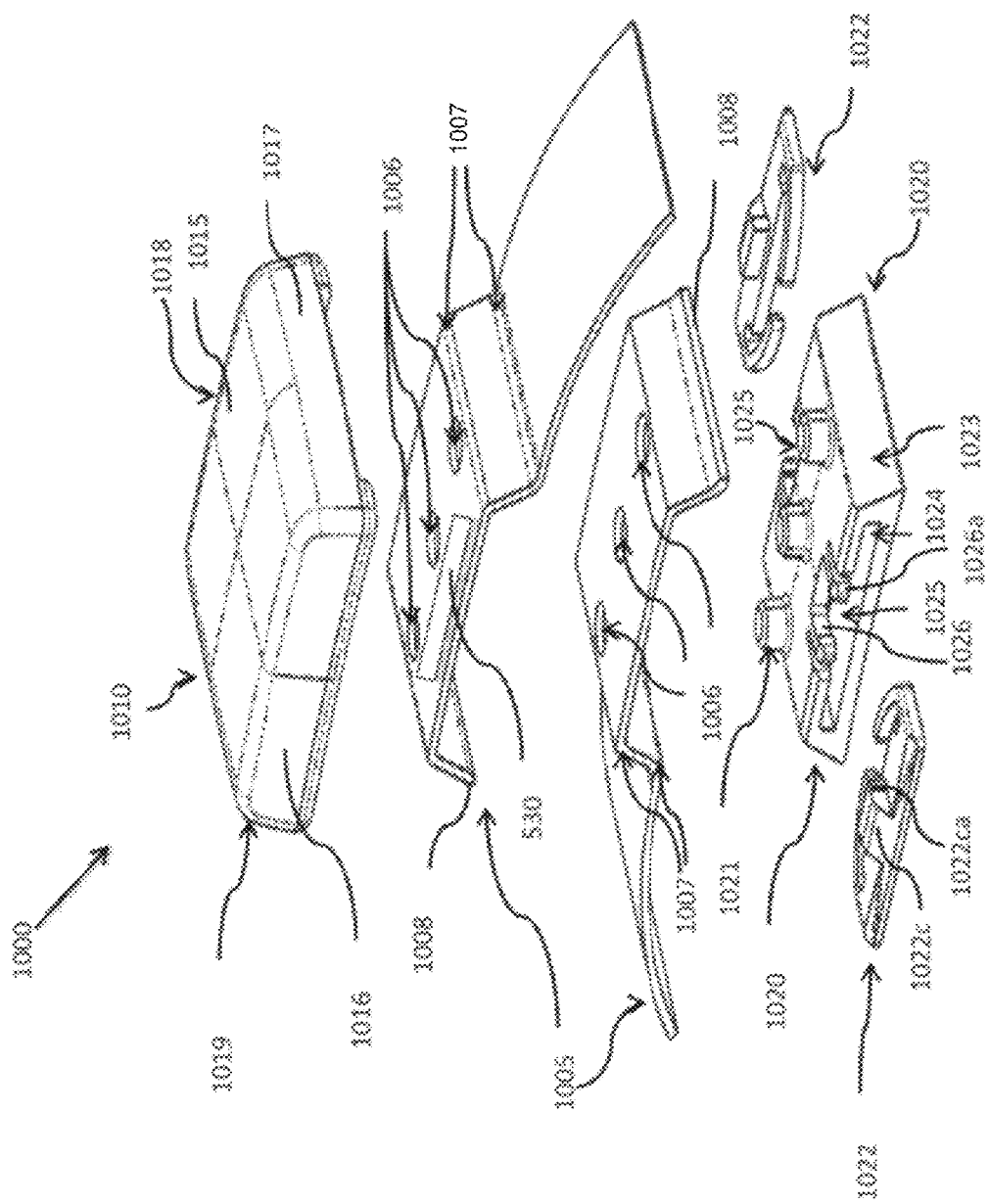
FIG. 11 is an exploded view of the clasp and partial portion of the wristband of FIG. 1, in accordance with an embodiment of the disclosed subject matter.

FIG. 11 is an exploded view of the clasp and partial portion of the wristband of FIG. 10, in accordance with an embodiment of the disclosed subject matter. In FIG. 11, the clasp 1010 has a number of features that make it highly resistant to tampering once it is assembled. In general, the clasp parts can be made of plastic, composite, metal or some combination of dissimilar materials although the clasp embodiment shown in the figures has a special advantage of having an all-plastic construction. Non-metal parts are preferred and required in many settings such as corrections facilities where metal parts can be weaponized in some improvised fashion. However, plastic is orders of magnitude less stiff than metal so it presents special challenges for making tamper resistant clasps. Embodiments of the disclosed subject matter overcome the inherent limitation of plastic parts in making a tamper resistant clasp by virtue of several key features. For example, the top portion 1010 of the clasp 1001 surrounds the bottom 1020 of the clasp 1001 and wristband 1005 on five sides. Once snapped into place, the top portion 1010 of the clasp 1001 also fits very tightly over the rest of the assembly such that there are no visible gaps at the intersections of the clasp parts or wristband exits. Having five sides to the top portion 1010 of the clasp 1001 greatly increases its stiffness and resistance to deformation and failure from prying tools. This added stiffness is especially important with plastic parts since their resistance to deformation is much lower than with metal parts. Having five sides to the clasp top also forces the wristband 1005 to have a more tortuous path before it exits the body of the assembled clasp. As shown in FIG. 11, having side four 1017 and side five 1019 on the top portion 1010 of the clasp 1001, forces the wristband to have two bends 1007 prior to exiting the assembled clasp 1001. This tortuous path prevents a prying tool from entering deep into the center of the clasp 1001 and gaining substantially more leverage to break or deform the clasp 1001. The sloping surface 1023 of the bottom portion 1020 of the clasp 1001 also forces the wristband 1005 to snuggly conform to the clasp 1001 with no visible gaps which further prevents tools from penetrating deep into the clasp 1001 to gain pry leverage. The two bends 1007 in the wristband's 1005 path shortens the lever arm a pry tool has, which greatly increases tamper resistance.

In FIG. 11, two recessed clips 1025, each with a pair of flexible finger elements 1026 with inwardly flanged ends 1026a, are formed on the middle edge and on opposite sides of the top side of the bottom portion 1020. The recessed clips 1025 are configured to receive and slidingly connect to an anchor post 1022c on the top of each non-retractable spring slide 1022 when the non-retractable spring slides 1022 are pushed into the opposite longitudinal grooves 1024. Similar to the flexible finger element inwardly flanged ends 1026a, the anchor posts 1022c have outwardly flanged ends 1022f, which are configured to slidingly engage the flexible finger elements 1026 of the non-retractable spring slides 1022, but not be removable from the recessed clips 1025. The anchor posts 1022c on the top of each non-retractable spring slide 1022 clip are configured to slide between the flexible finger elements 1026 and mate into the recessed clips 1025, To facilitate this mating the leading, outer edges of the anchor posts 1022c are angled and the flexible finger element flanged ends 1026a are vertically chamfered to meet the angled, leading, outer edges of the anchor posts 1022c to help push the flexible fingers 1026 apart and permit the flanged end 1022f of the anchor posts 1022c to push through and into the recessed clips 1025 and are prevented from being removed by the inwardly flanged ends 1026a of the flexible fingers 1026. The two non-retractable spring slides 1022 act as locking devices to hold the clasp mechanism together when the bottom portion 1020 is inserted into the top portion 1010 of the clasp 1001. The wristband 1005 can be used to hold an RFID or biosensor beacon, for example, but not limited to, the RFID beacon device 530 discussed above in relation to FIG. 5, on a person's wrist. The beacon device 530 can slide onto or otherwise be fastened to the band in such a way that it cannot be removed without destruction of the wristband, clasp and/or beacon.

There are many settings where patients or other internees must wear wristbands for a variety of reasons but the patients are non-compliant or will remove, alter or destroy a typical wristband. In these situations, a tamper-resistant wristband, as shown in FIGS. 10 and 11, is needed. One or more embodiments of the disclosed subject matter address the need for a wristband 1005 that can be worn in an inpatient setting such as a psychiatric hospital, correctional facility or any facility where there is a need for a tamper-resistant wristband that can only be removed destructively. In other words, the wristband has a one-time use. Wristbands are needed for patient identification purposes or to attach RFID, biosensor or other types of wearable electronic beacon devices 530. Such inpatient facilities typically also restrict the use of metal components because of the potential for improvised weaponization or self-harm. Therefore, there further exists a need for a tamper-resistant wristband made entirely or largely out of plastic or non-metallic materials, especially the wristband 1005 and clasp 1001 used to secure the wristband 1005 ends. Embodiments of the disclosed subject matter deal with a tamper-resistant one-time use disposable clasp 1001 that typically must be removed by cutting the wristband 1005, which is also disposable and one-time use.

There are numerous situations where it is useful to be able to attach a band or strap onto a person's wrist or ankle and have it be impossible for them to remove it without cutting the strap. Hospitals, security facilities, and other secure areas use bracelets or bands that achieve this. However, most existing designs can be opened with basic tools such as a screwdriver or kitchen utensil. Embodiments of the disclosed subject matter describe a one-time use clasp 1000 that cannot be opened with basic or improvised tools.

For example, the user puts the preassembled bottom portion 1020 of the clasp 1001 on the wearer's wrist. The strap 1005 with pre-punched holes 1006 is sized and placed onto multiple security pins 1021 located on a top side of the bottom portion 1020. The person applying the device then presses the top housing onto the top and optionally trims any excess band material 1005. During closure, the pathway of the clasp tightens the band slightly due to the jogs in the path.

The clasp 1001 has three major security features. The first is that the top portion 1010 of the clasp 1001 surrounds the bottom portion 1020 of the clasp 1001 on five sides. This provides additional strength to the design. The second feature is that the path that the band takes is not straight. There is at least one bend, and preferably two bends in this path. This prevents tools from entering the core of the clasp. The third feature is that the slides that engage when the clasp is closed are separate or integrated features that are spring loaded and non-retractable. These slides can be spring loaded with plastic or metal spring features.

In some embodiments, the top portion 1010 of the clasp 1001 can be tethered to the bottom portion 1020 of the clasp 1001. The slides are generally pre-assembled to the bottom portion 1020 of the clasp 1001.

The current embodiment also has a near zero force required for closing and securing the clasp. The design also requires almost no training. Both of these requirements are critical for the clasp is used widely with a wide range of human capabilities (hand size and strength, aptitude, etc.).

Figure 12:
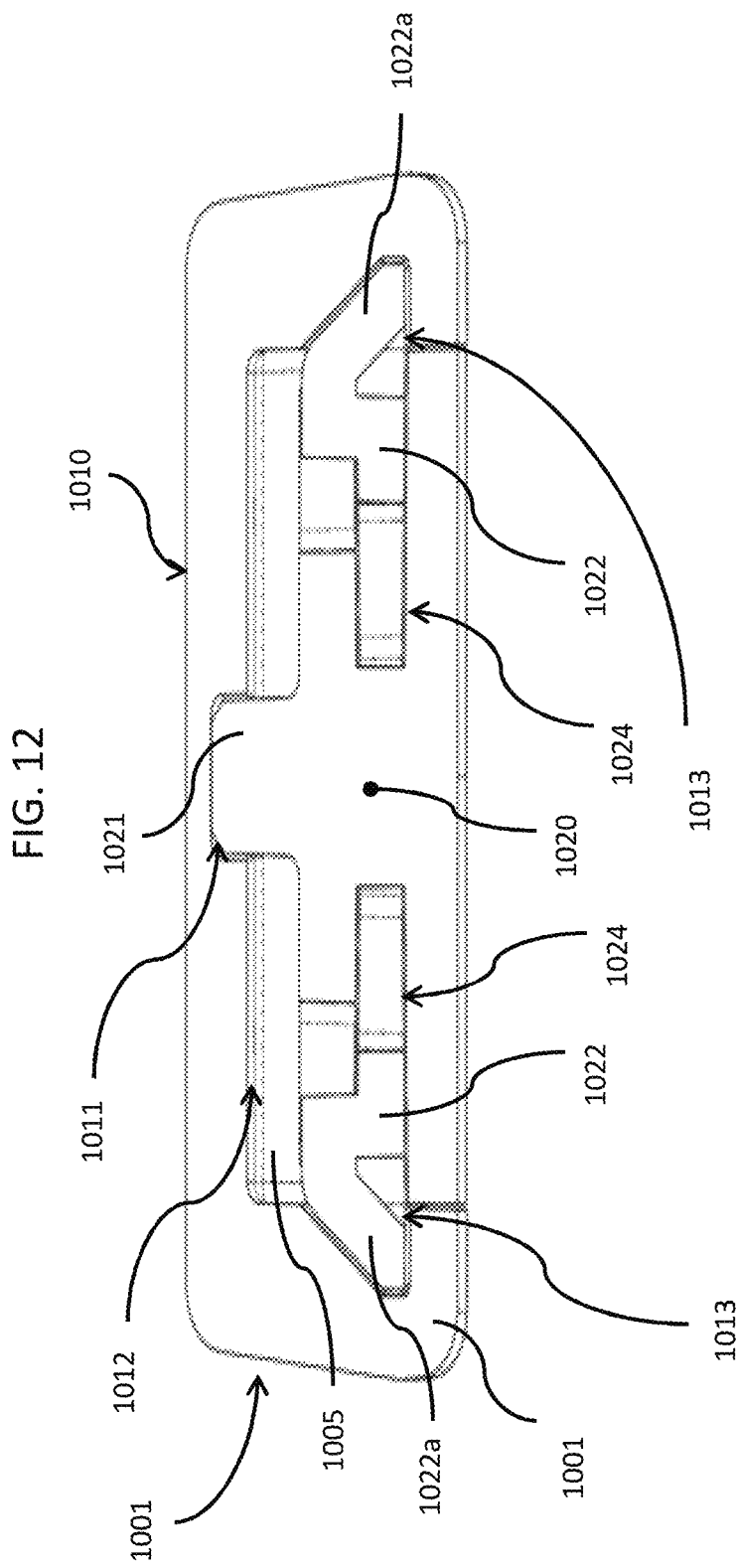
FIG. 12 is a cross-sectional view of the clasp portion of FIG. 10 along line A-A, in accordance with an embodiment of the disclosed subject matter.
Figure 13F:
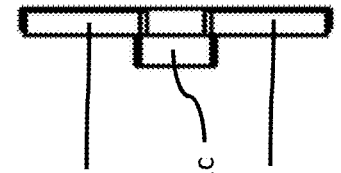
FIGS. 13A-13G include top, bottom, back side, left side, right side, front side and a top perspective views of the non-retractable spring slides of the non-retractable spring slide of FIG. 11, in accordance with an embodiment of the disclosed subject matter.
Figure 13E:
Figures 13B, 13C:
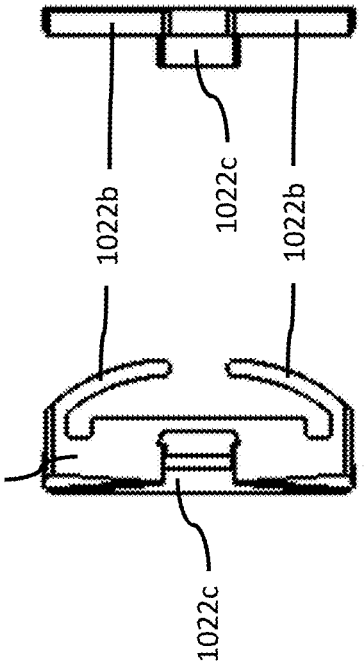
Figure 13D:
Figure 13A:
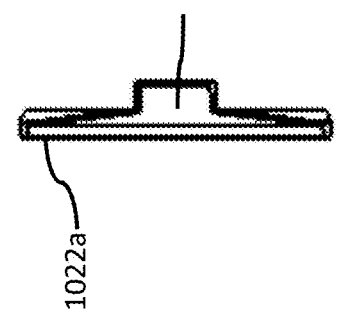
Figure 13G:
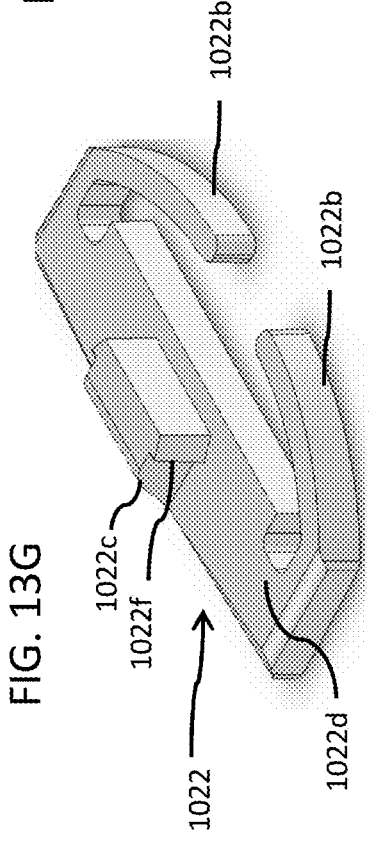

In FIG. 11, once the beacon device 530 is slid onto or attached to the wristband 1005, the bottom portion 1020 is attached to the wristband 1005 by placing the plurality of openings 1006 at each end 1008 of the wristband 1005 over the mounting/security pins 1021 on the top of the bottom portion 1020. Then the bottom portion and wristband 1005 are attached to the top of the clasp 1010 by inserting the bottom portion 1020 of the clasp 1001 into the top portion 1010 of the clasp 1001 so that the mounting/security pins 1021 engage and fit into a plurality of reciprocally-shaped mounting holes 1011 in the bottom of the top surface of the top of the clasp, which is best seen in FIG. 12, and which slide onto the mounting/security pins 1021 on the bottom of the clasp. Returning to FIG. 11, the wristband 1005 with beacon device 530 and pre-assembled bottom portion 1020 is placed on the person's wrist and fastened on the wrist by wrapping the loose end of the band over the mounting/security pins 1021 and snapping the top portion 1010 in place so that the spring slides permanently lock into place in the top portion 1010. When the current embodiment of the clasp, which uses the pins 1021 to engage the openings 1006 in the wristband 1005, is exposed to >350 lbs., the clasp 1001 remains undamaged and retains its closure. The wristband 1005 can only be removed from the wearer's wrist by cutting the band or otherwise destroying the band, clasp and/or beacon.

Embodiments of the wristband 1005 can be composed of any organic, inorganic or combination of dissimilar materials. However, for controlled environments such as inpatient psychiatric hospitals and corrections facilities where metal tools are not present, the band material is designed to resist chewing, tearing, abrasion, or destruction by improvised tools. Polyester, Kevlar or some combination of polymer materials in a variety of woven, knitted configurations, injection molding and/or implant molding can be used as the wristband materials. The wristband 1005 can also be made of metal or dissimilar materials where one of the components is metal. However, metal can introduce additional risks for self-harm by certain populations wearing the wristband. The wristband can be universally sized to fit a wide distribution of wrist and ankle sizes. Although a variety of means can be used to secure the wristband 1005 to the clasp 1001, in the current embodiment in FIG. 11, the wristband 1005 has the plurality of holes 1006 punched in both ends of the band for mounting over the mounting/security pins 1021 on the bottom portion 1020 of the clasp 1001. The other end typically has many holes to allow for customized sizing to the wearer's extremity. Typically, once the band 1005 is sized to the wearer, the excess band material is cut flush with the edge of the assembled clasp 1001.

As seen in FIG. 11, the two sides 1017, 1019 where the wristband 1005 exits the clasp 1001 force the wristband 1005, in the current embodiment to have two bends 1007 prior to exiting the clasp. This tortuous, in-direct path greatly shortens the lever arm that a pry tool has to force open the clasp 1001. In addition, there are zero gaps at all mating intersections of the parts and wristband. This makes it more difficult for tools to enter especially an improvised tool where a very thin and stiff tool would be needed. Sloped surfaces 1014 (see FIGS. 14A and 14H), 1023 on the top portion 1010 and the bottom portion 1020, respectively, of the clasp 1001 help to form the bends 1007 in the wristband 1005 and to tightly conform to the wristband's 1005 path thereby preventing gaps for a tool to penetrate.

In FIG. 11, as well as in FIG. 12, the non-retractable spring loaded slides 1022 that can be integrated and/or pre-assembled into the opposite longitudinal grooves 1024 formed in the sides of the bottom portion 1020 of the clasp 1001, which engage slots or indents 1013 in the inside of the longitudinal side walls 1016, 1018 of the top portion 1010 of the clasp 1001. Spring arms 1022b of the non-retractable spring loaded slides 1022 provide spring loading forces to bias or push the slides 1022 away from the opposite longitudinal grooves 1024 formed in the sides of the bottom portion 1020 and toward the slots or indentations 1013 formed in the sidewalls of the top portion 1010 of the clasp 1001. In addition to locking the clasp 1001 together, this helps to block any pry tool entry and to stay engaged with the top portion 1010 of the clasp 1001 even with some deformation of the top portion 1010 of the clasp 1001.

In this embodiment, the clasp is design as an integrated disposable beacon device 530 housing, which permits the disposable beacon device 530 to be combined with the clasp 1001. For example, but not limited to, the integrated disposable beacon device 530 can be water-resistant to >1 meter static water pressure, crush proof to >500 lbs., and impact and drop resistant.

Embodiments using this design are especially effective for an all-plastic clasp since plastic parts are much less stiff than metal parts and are therefore inherently harder to make into a tamper-resistant clasp. In addition, metal is also banned or restricted in many settings such as Corrections or psychiatric facilities, so all plastic clasps are needed.

FIG. 12 is a cross-sectional view of the clasp portion of FIG. 10 along line A-A, in accordance with an embodiment of the disclosed subject matter. In FIG. 12, the latitudinal cross-sectional view shows the engagement of the components of an assembled clasp. For example, one of the mounting or security pins 1021 is seen inserted into one of reciprocally-shaped mounting holes 1011 that are formed in an underside of the top portion 1010 of the clasp 1001. In addition, a cross-section of the wristband 1005 is seen between the underside of the top portion 1010 and a top side of the bottom portion 1020 with an open area 1012 between the underside of the top portion 1010 and a top side of the wristband 1005. This open area 1012 is used to provide space for the beacon device 530.

As seen in FIG. 12, an outer leg portion 1022a of each of the two non-retractable spring slides 1022 are engaged in the slots or indentations 1013 formed in the inside of the sidewalls 1016, 1018 of the top portion 1010 and in the opposite longitudinal grooves 1024 formed in the sides of the bottom portion 1020 to lock the clasp 1001 and wristband 1005 together. The non-retractable spring slides 1022 block a pry tool from penetrating deep into the clasp and gaining leverage to deform or break the clasp. The spring-loaded aspect of the non-retractable spring slides 1022 forces the non-retractable spring slides 1022 to stay retained and engaged with the walls of the top portion 1010 of the clasp 1001 even if there is some deformation of the top portion 1010. In embodiments of the disclosed subject matter, the non-retractable spring slides can span the length of top portion 1010 wall in a contiguous fashion or as a series of independent, discrete features.

FIGS. 13A-G show top, bottom, back side, left side, right side, front side and a top perspective views of the non-retractable spring slide of the non-retractable spring slide of FIG. 11, in accordance with an embodiment of the disclosed subject matter. In FIGS. 13A-G, spring arms 1022b are seen extending outwardly away from opposite outer edges of a body portion 1022d of the non-retractable spring slide 1022 and then curving inwardly toward each other to form an arced shape with an open area between inner ends of each spring arm 1022b. In addition, the outer leg portion 1022a of each non-retractable spring slide 1022 is sized and configured to fit into one of the slots or indents 1013 formed in the inside of the longitudinal walls 1016, 1018 of the top portion 1010 of the clasp 1001. As noted above, the non-retractable spring slides 1022 act to lock the top portion 1010 and the bottom portion 1020 of the clasp together and prevent efforts to separate the two once locked together to form the clasp 1001.

FIGS. 14A-H includes top, bottom, back side, left side, right side, front side views, a longitudinal cross-sectional view along line B-B and a top perspective view of the clasp top body portion of the clasp of FIGS. 10 & 11, in accordance with an embodiment of the disclosed subject matter. In FIGS. 14A-H, the reciprocally-shaped mounting holes 1011 in the bottom of the top surface of the top portion 1010 of the clasp 1001 can be best seen in FIGS. 14A, 14G and 14H. In addition, how the five sides of the top portion 1010 are configured to connect to the bottom portion 1020 and prevent tampering is best seen in FIG. 14G. Specifically, in FIGS. 14D, 14E and 14G, it can be seen how the bottom, inside surfaces 1016a, 1018a of the longitudinal sidewalls 1016, 1018 are configured to abut the longitudinal sides of the bottom portion 1020 and form a smooth, outside bottom surface of the clasp 1001 that is resistant to tampering and efforts to open the clasp 1001.

FIGS. 15A-G includes top, bottom, back side, left side, right side, front side views and a top perspective view of the clasp bottom body portion of the clasp of FIGS. 10 & 11, in accordance with an embodiment of the disclosed subject matter. In FIG. 15A, a top view of a bottom side 1028 of the bottom portion 1020 is shown. In FIG. 15G, the flexible fingers 1026 and inwardly flanged ends 1026a of the flexible fingers 1026 are more clearly shown.

FIGS. 16A-G includes top, bottom, back side, left side, right side, front side exploded views and a top perspective exploded view of the clasp portion of FIGS. 10 & 11, in accordance with an embodiment of the disclosed subject matter. In FIG. 16A-G, the different views of the clasp 1001 are shown without the wristband 1005 to more clearly illustrate the configuration and assembly of the clasp 1001.

FIGS. 17A-G includes top, bottom, back side, left side, right side, front side views and a top perspective, cross-sectional view along line C-C of the clasp portion of FIGS. 10 & 1, in accordance with an embodiment of the disclosed subject matter. In FIGS. 17A-G, the clasp 1001 is shown fully assembled, but without a wristband 1005. In FIGS. 17A-F, the top, bottom, back side, left side, right side, front side views of the assembled clasp 1001 are shown. FIG. 17G is partial cutaway view of FIG. 17C along line C-C to show the inner configuration and interrelationships between the top portion 1010, the bottom portion 1020 and the non-retractable spring slides 1022.

As previously discussed, RF signals are often used in a variety of configurations to determine the relative or absolute position of one or more objects, people or things. Position can be determined by triangulating signal strengths amongst a collection of transceivers whose position is known. Infrared or ultrasound signals can also be used in a similar fashion or in combination with RF. Typically, these technologies create a probability of location or proximity due to the variability of such signals, which can result in poor system performance, response times and efficiencies. However, these systems are complicated and expensive because they involve some degree of infrastructure, calibration and maintenance.

Therefore, there exists a need for a simpler means of determining the proximity between two or more objects, people or things where each of the entities has a transmitter, receiver or transceiver. The two entities can be mobile and/or stationary. However, radio frequency signals are inherently variable due to direct and multipath transmissions. This inherent variability complicates any correlation between RF signal strength and proximity (distance) especially if triangulation is not being used and the measurements are point-to-point between User and patient. If the transmission rate of the RF signal is seconds or milliseconds and you are relying on a threshold signal strength to have a person make a decision, as opposed to software making the decision, via some visual or audio trigger, the threshold level can change too rapidly not only for a person to make a decision, but to even be notified that a decision needs to be made. This is especially true if the user has multiple patients/beacons to monitor via visual or audio triggers.

Two known techniques used to address such signal variability and set the threshold value include: averaging a group of signals; and binning a group of consecutive signals and selecting the maximum signal from that bin. Averaging and binning have a common problem when you are relying on a human user to react (make a decision) to a direct or software generated request for action. By definition these techniques use historical or past information. When using historical information, the system cannot rely on a human user to wait or stay on station with their patient until the request for action comes through again, because the user may have moved on from the patient to another patient or the patient may have moved away from the user. This is especially true, if the RF signal levels are highly variable compared to the optimal time needed for the human user to take a requested action. Regardless, processor and system performance can be degraded or inhibited due to the use of historical data that opens an entry window for a patient that the user has already moved past or has moved away from the user, so it not would be a valid observation entry. Fortunately, this would not prevent the user from entering information for another patient that the user is actually observing, but the user would have to be and remain in range of and receive a beacon signal from the other patient to give the processor time to determine proximity and open a window for the other patient. As a result, not only is the system wasting processing resources waiting for information on the past patient, but making the user wait for the system to catch up and detect the other patient actually being observed by the user. Not only does this waste processor/system resources it also wastes human resources in a setting that cannot afford to be inefficient.

In embodiments of the disclosed subject matter, this problem is solved by having the system software detect when the RF signal threshold level has been reached indicating that a patient is in range of a T/R and then hold the visual or audio cue for some predetermined/predefined period of time so that the user of the T/R has sufficient time to make a decision. In other words, embodiments of the disclosed subject matter do not rely on historical data.

Figure 18:
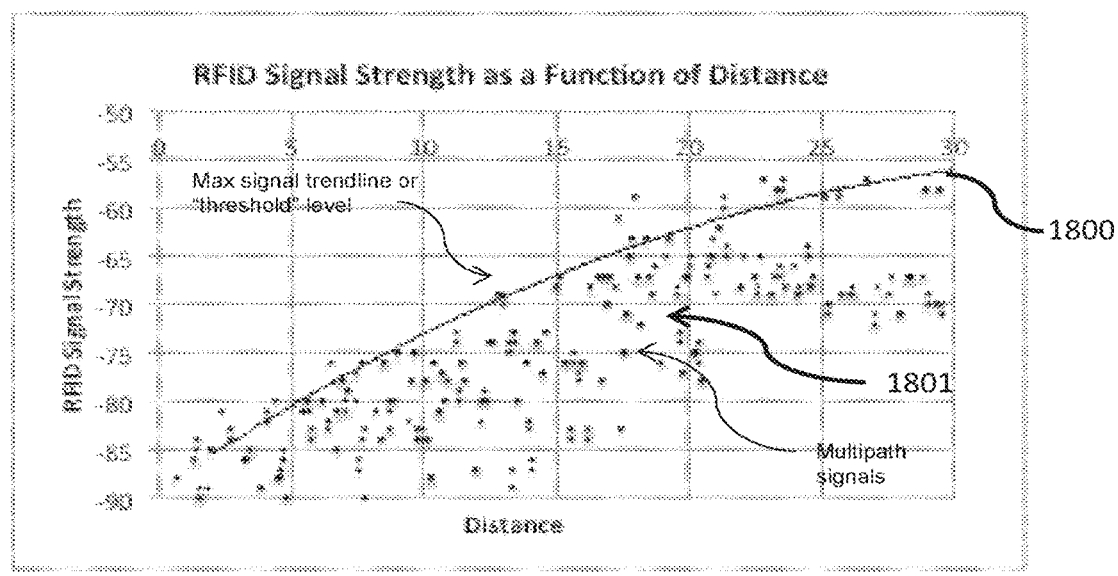
FIG. 18 is a chart showing the RFID signal strength as a function of distance from an RFID beacon, in accordance with an embodiment of the disclosed subject matter.
Figure 21:
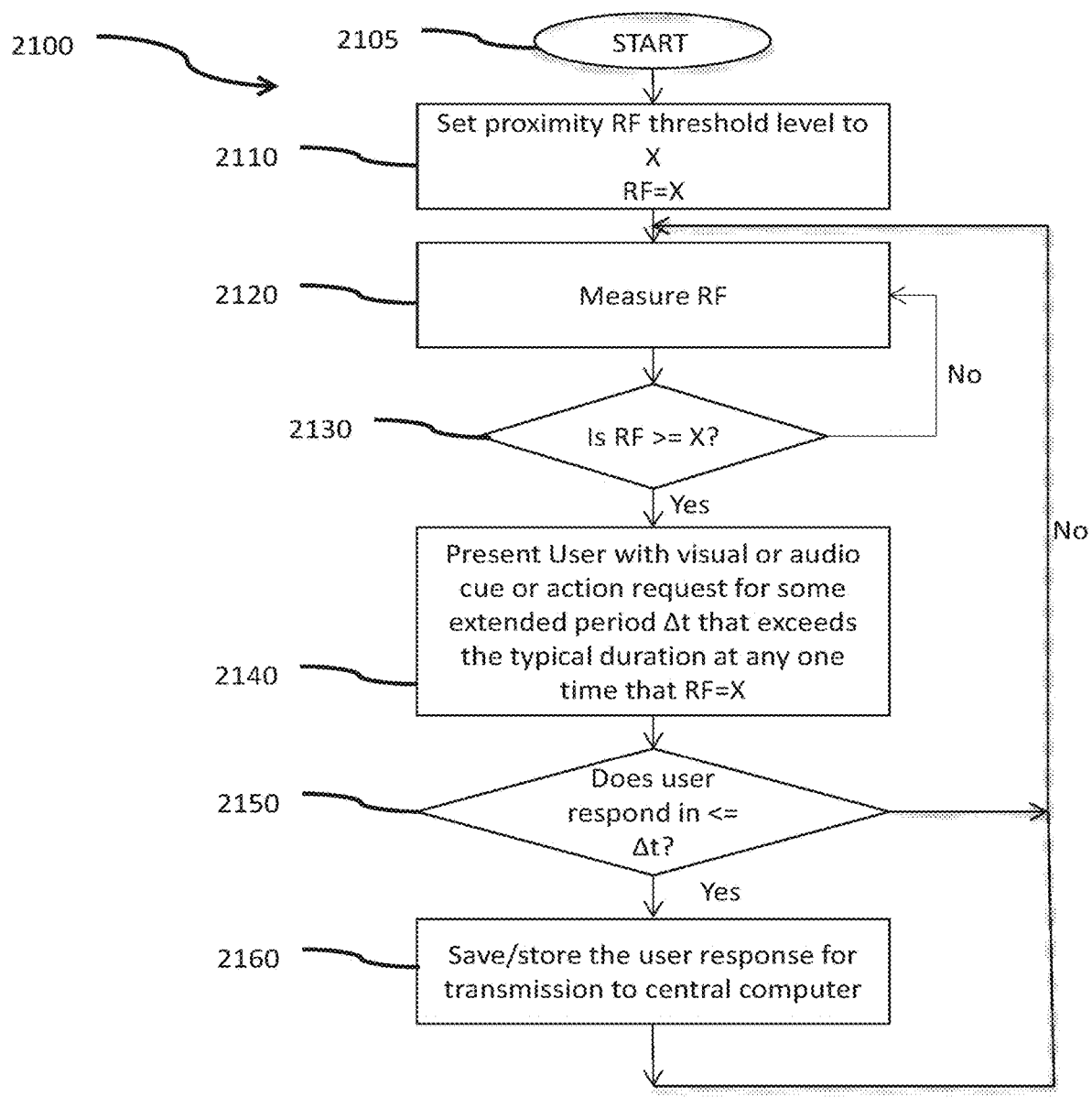
FIG. 21 is a logic flow chart of a system algorithm used for making decisions that a patient wearing a beacon and clasp of FIGS. 10 & 11 are used, in accordance with an embodiment of the disclosed subject matter.

FIG. 18 is a chart showing the RFID signal strength as a function of distance from an RFID beacon, in accordance with an embodiment of the disclosed subject matter. RF signals traveling to an RF receiver vary in intensity as shown in FIG. 18. There will be a maximum level of signal transmission strength 1800 that forms an envelope 1801 over many transmission points that vary in intensity. The maximum signal transmission strength 1800 points can be correlated to proximity between transmitter and receiver. Knowing this correlation, one can select a threshold signal strength approximately equal to the maximum level of signal transmission strength 1800 to determine an approximate proximity. However, as shown in FIG. 18, measurement of the signal strength can be unstable due to the multipath points. Multipath signals typically are not direct line-of-sight signals, which represent a maximum signal level and which forms the maximum signal transmission strength 1800 envelope. Multipath signals 1801 reflect off one or more surfaces before hitting the signal receiver where their power level is registered. Attempting to use the maximum signal level to trigger a visual or audio cue or decision request for a user, will likely not provide the user with enough time to take the requested action, especially if the time to respond is tied to the duration of maximum signal since the threshold level will be unstable and brief. As a result, the system will be inefficient and waste system processing resources due to useless context switching cycling back and forth from a received signal that exceeds the signal threshold to one that does not exceed the signal threshold. This can occur, because turning on the system's ability to accept a required input from the user after receiving a signal that exceeds the threshold value to then turning it off as soon as the next signal is received that is below the threshold level. In addition, due to the short time between transmission of the individual signals, the amount of time a user would have to make the necessary entries In embodiments of the disclosed subject matter, this problem is solved by presenting the user with the decision request for a predetermined/predefined period of time ($\Delta T$) that is typically longer than the duration of time where the maximum signal level is present, as shown in FIGS. 18, 19 and 21. FIG. 19 is a time line showing the time a user has to respond to a software request received as a result of the proximity of a beacon and associated clasp to a user with a mobile sensor device of FIGS. 10 & 1, in accordance with an embodiment of the disclosed subject matter. In FIG. 19, once a beacon signal exceeds the threshold level (X), the software presents the user with a request for action for a time interval equal to the beacon signal advertisement time interval Y and an additional predetermined/predefined time interval K. Time interval K can be set to be equal to or greater than the minimum period of time for a user to respond to a software or direct (digital or analog direct sensor feedback) request for action via some visual or audio trigger. In addition, time interval K can also be set as a multiple of the beacon signal time Y, or the beacon signal time Y plus a predetermined/predefined time period that has been specified and/or determined to be a minimum and/or average time that is needed for the user to recognize the alert and enter the necessary information for the identified patient into a portable device, for example, but not limited to, the observer T/R 120, the central computer 130, and the PDAs 150.

In FIG. 19, if the system were to only permit the user to respond during the time of the signal detection, the system would become inefficient and/or unusable. For example, as discussed above and seen in FIG. 18, and as seen here in FIG. 19, because of the inherently variable nature of RF signals due to the direct and multipath transmissions, it is not uncommon to not receive continuous RF signals that exceed the threshold level. As a result, the system processor can start context switching cycling when it receives a signal with RF greater than or equal to (i.e., ">=") X and sends out a request to the user, but then the next RF signal received is NOT>=X, so the system immediately closes out the request and either won't accept any input from the user or only receive a partial input. If this continues to happen, the processor will begin to become inefficient and potentially get caught in extended or endless context switching loops during which time, nothing can be entered into the system. If the signal advertisement time is short enough, for example, only milliseconds or seconds, and there is not a continuous stream of signals with RF>=X in continuous advertisement periods, then, the system either may not have enough time to display the request or the request may be displayed, but then it is revoked before the user can see it and/or respond to it. If any of these situations occur, the system can become so inefficient that it is only barely useable or not useable at all. As described below, embodiments of the disclosed subject matter help resolve this system performance problem.

Figure 20:
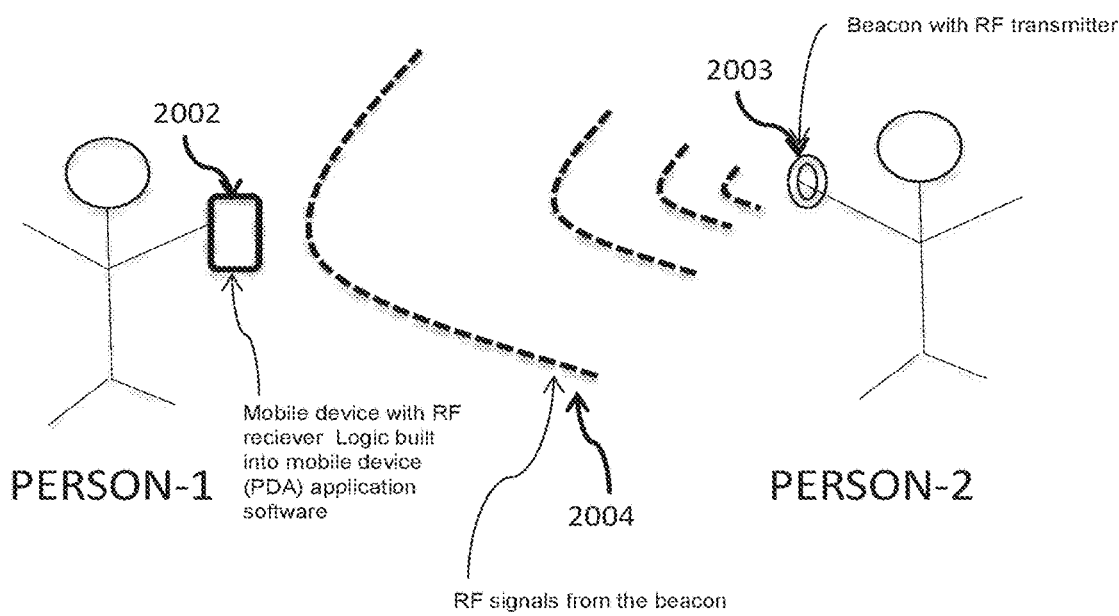
FIG. 20 is a representation of the interaction of the two users of a system in which embodiments of the clasp and wristband of FIGS. 10 & 11 are used, in accordance with an embodiment of the disclosed subject matter.

FIG. 20 is a representation of the interaction of the two users of a system in which embodiments of the clasp and wristband of FIGS. 10 & 11 are used, in accordance with an embodiment of the disclosed subject matter. For example, in FIG. 20, the maximum signal level 2004 being sent by a beacon 2003 on a patient, may only be present for milliseconds or seconds but, regardless, it is much less time than is needed for the software in a mobile device 2002, for example, but not limited to, a PDA, to present a request for action to a user and then for the user to respond to the requested action. However, by presenting and holding open the request for action for an extended period, for example, but not limited to, K+Y time, the user will have adequate time to respond. While this novel methodology can be used with any kind of RF, infrared or ultrasound signal, it is especially useful under the following conditions. The embodiment in FIG. 20 can use standard off-the-shelf mobile devices that have the built-in ability to receive Bluetooth signals and no need for multiple facility based Wi-Fi-Bluetooth transceivers to measure and relay proximity information. As a result, not only is the necessary system hardware simplified, but the signal detection and processing is simplified, which results in a more efficient and responsive system.

The RF in FIG. 20 can be Bluetooth and the user (e.g., a human) is making a decision rather than the software. The user is using a mobile device to directly interrogate multiple patient beacons each with a unique Bluetooth address. However, the user is not "linking" with each beacon for which it receives a signal 2004. Instead, the user is simply measuring the strength of each beacon's received advertising signal against the RF threshold value 1801 to determine proximity to that particular patient.

In other embodiments of the disclosed subject matter, the interrogation of the patient beacons via a mobile device can also be indirect. That is, a series of Bluetooth or RF receivers can be positioned in a facility, room or chokepoint to collect the patient's Bluetooth signal and determine the patient's position relative to a user with a mobile device. The User and patient's position can be reported via Wi-Fi.

The algorithm or logic for determining when a patient is in range and thereby modifying the user's mobile/PDA display accordingly can be executed on the mobile/PDA application software. However, the algorithm can also be executed in a central server or a Cloud server and the user's display changed via commands delivered to it via Wi-Fi.

FIG. 21 is a logic flow chart of a system algorithm used for making decisions that one or more patients wearing a beacon and clasp of FIGS. 10 & 11 are within range of an observer's signal detection and information recordation device, in accordance with an embodiment of the disclosed subject matter. In FIG. 21, a process 2100 for detecting a beacon advertisement signal begins 2105 and sets 2110 a proximity RF threshold level to a value X where any detected signals greater than or equal to X will be considered to be "in range". The process continues and measures 2120 the level of a received RF signal and then determines 2130 whether the received RF signal is greater than or equal to the threshold level X (i.e., RF>=X). If RF<X, then the process loops back to measure 2120 a next received signal. If it is determined 2130 that the RF>=X, then, the system presents 2140 the user with a visual or audio cue or action request for an extended period of time Δt that exceeds the advertisement period of the detected signal for which RF>=X. The system then determines 2150 whether the user responds with the information before the end of the extended period of time Δt. As described above, each signal is associated with a specific patient, so the information requested is for the patient associated with the detected signal. If it is determined 2150 that the user does NOT respond before the end of the extended period of time Δt with the information for the patient associated with the detected signal, then the process returns to measuring 2120 the received RF signals. If it is determined 2150 that the user does respond before the end of the extended period of time Δt with the information for the patient associated with the detected signal, then the process saves/stores 2160 the information in the user device and, when appropriate, transmits it to the central computer, which can be essentially immediately after the information is received, or at a preset later time, or manually after the user returns to the central computer. Regardless, of when or if the saved/stored information is sent to the central computer, after it is saved/stored in the user device, the process returns to measuring 2120 the received RF signals. Alternatively, although not explicitly shown in the process, instead of returning to measuring 2120 after the information is saved/stored 2160, the process can end. The process described in FIG. 21 is designed to resolve the above-described inefficiency and context switching cycling issues that can occur with the use of RF signals.

In the description of FIG. 21 provided above, for clarity of understanding, the system was described in terms of detecting a beacon signal from a single beacon with RF>=X. Of course, the system is more complex and can detect and simultaneously receive, process and act on multiple beacon signals from multiple different beacons with RF>=X. For example, in one non-limiting example, after the initial detection of the first beacon signal with RF>=X, the observer T/R can and does continue to detect multiple beacon signals with RF>=X. These signals can come from the same beacon as the first beacon signal that was detected, as well as multiple other beacons. Unfortunately, an observer can only enter information on one patient at a time into the observer T/R. If any of the detected beacon signals with RF>=X are detected for the first detected beacon, the currently allocated time to receive input from the observer can be immediately extended or a flag can be set or value stored to extend the time for a response from the observer, if it is needed. If not needed, the information can be cleared upon the receipt of the information from the observer.

Alternatively, and also as a non-limiting example, after the initial detection of the first beacon signal with RF>=X, the observer T/R detects one or more beacon signals with RF>=X, but the one or more signals this time come from different beacons. Because the observer is already entering information on the one patient associated with the first detected beacon signal into the observer T/R. If any of the detected beacon signals with RF>=X are detected for other beacons, one or more flags can be set or values stored to indicate for which other beacons signals with RF>=X have been received and in what order. As soon as the system is free after the entry of the information for the first signal, the system can pull the next sequentially detected signal from the list, determine how much of the predetermined time it would have left to request and receive the information for that patient and, if sufficient time remains, request and then wait to receive the information. While the other detected signals are waiting, they too can be updated with additional time should additional signals of sufficient strength be detected coming from that same beacon. Alternatively, rather than taking the next in line detected signal, it could be more advantageous to take the latest detected signal. This can be true for several reasons including, for example, but not limited to, the last received signal is the most likely to have the longest time remaining to receive the requested response and could be more likely that the observer is still near the patient associated with the new beacon.

Figure 22:
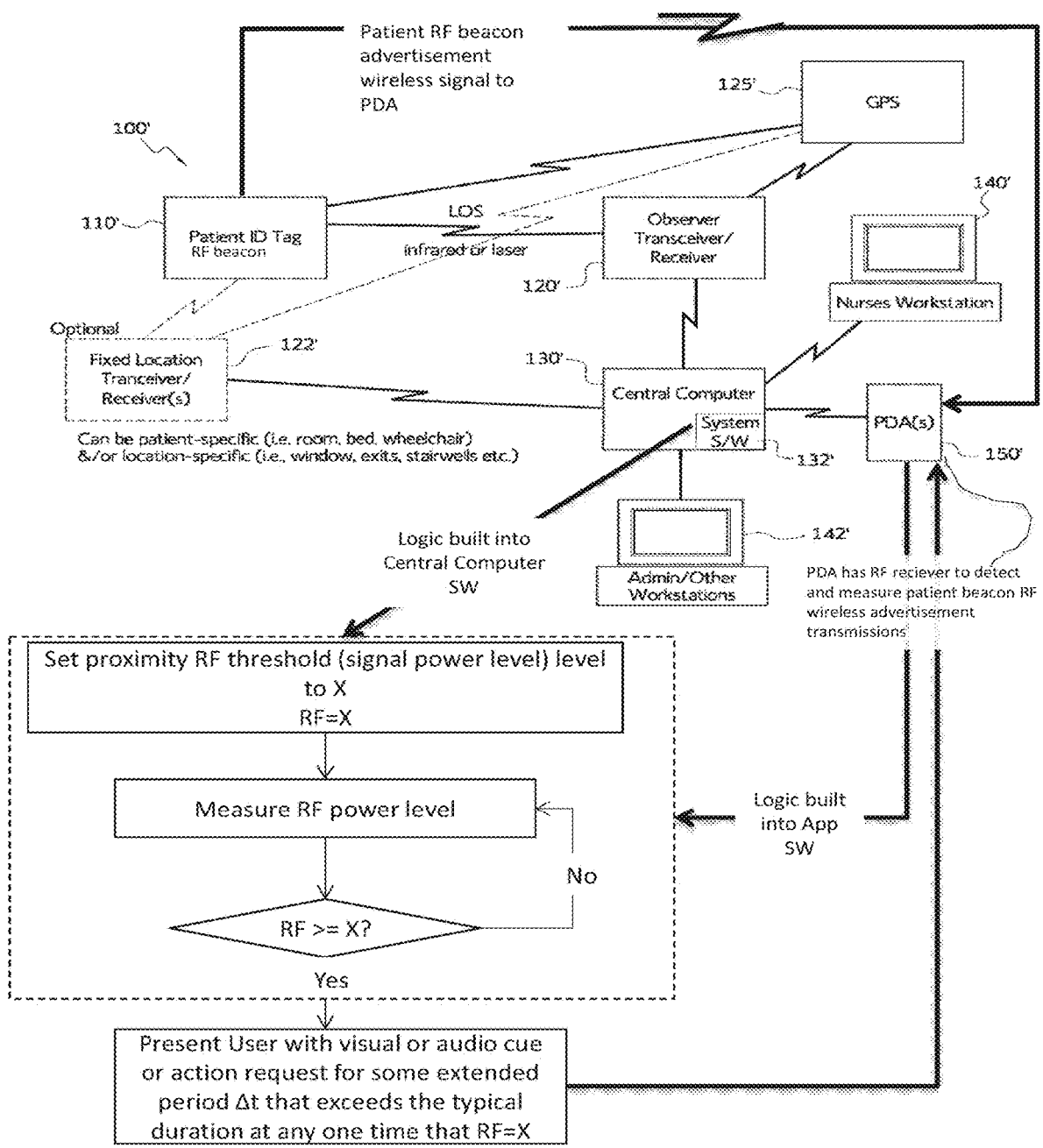
FIG. 22 is a combination block diagram of the electronic monitoring system using visual observation and RF signals from FIG. 1b and a flow chart illustrating the process followed by an observer to observe and monitor one or more patients using an electronic patient monitoring system and decision making process, in accordance with an embodiment of the disclosed subject matter.

FIG. 22 is a combination block diagram of the electronic monitoring system using visual observation and RF signals from FIG. 1*b* and a flow chart illustrating the process followed by an observer to observe and monitor one or more patients using an electronic patient monitoring system and decision making process, in accordance with an embodiment of the disclosed subject matter. In FIG. 22, the electronic patient monitoring system and decision making process used can also be the process shown in FIG. 21. Regardless of which embodiment of the electronic patient monitoring system and decision making process is implemented, in addition to being implemented in the observer T/Rs 120', it can be implemented in the central computer 130', the PDAs 150' and, if implemented, the fixed location T/Rs 122'. In FIG. 22, in addition to the method of operation described above for FIG. 1*b* for the T/Rs 120, 120' and which is also applicable to FIG. 22, the patient ID Tag 110' can also send a signal directly to the one or more PDAs 150' and the PDAs 150' can display the patient status information displayed on the observer T/Rs 120'. In turn, the PDAs 150' can be used by an observer to enter the requested information and then transmit it to the central computer 132'.

Figure 23:
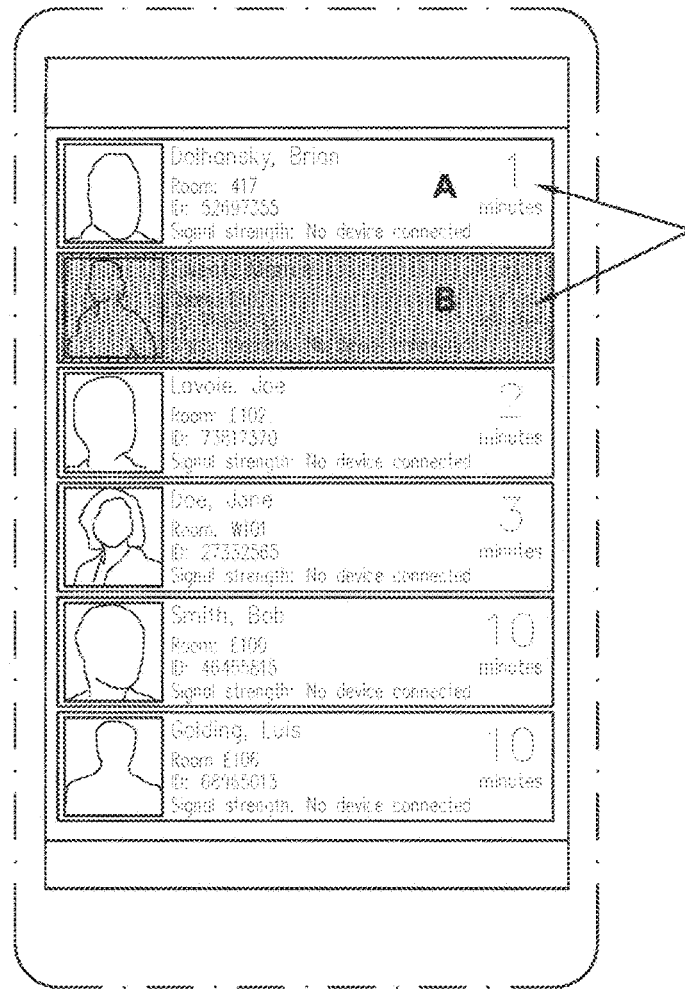
FIG. 23 is an extended combination block diagram of an electronic monitoring system using visual observation and RF signals and a flow chart illustrating the process followed by an observer to observe and monitor one or more patients using a hand-held device and the electronic patient monitoring system and decision making process of FIG. 22, in accordance with an embodiment of the disclosed subject matter.

FIG. 23 is a generic user screen that can be implemented on a PDA or other handheld device, for example, which is similar to that shown in FIG. 8b, in accordance with an embodiment of the disclosed subject matter. In FIG. 23, an example of a visual display a user with the PDA 150 or other handheld device can see, in general, and after a patient beacon RF transmission is received by the PDA with the RF signal equal to or greater than the RF power level set as the threshold X to indicate a patient is in range. In other words, when the RF beacon signal>=X. In this example, panel 'A' indicates a patient whose received RF beacon power transmission RF>=X, in which case, the display shows a 'white' background indicating that the patient is in range and the observer can enter the necessary observation information into the system. In contrast, patient 'B''s display is shown as a darker translucent overlay (shown in FIG. 23 as dark stippling). In this case, Patient 'B''s beacon transmission RF<X. In other words, patient 'B's beacon RF power transmission level is less than the power threshold set.

As described herein, patient 'A's power level might be >=the threshold X only momentarily and might not even register on the display without the implementation of an embodiment of the disclosed subject matter described herein. For example, Patient 'A's display will display as 'in-range' any patient for whom a signal was received with RF>=X, as shown in FIG. 23 for patient 'A', and the software will maintain the 'in-range' display for specified period of time delta t ($\Delta$t). For example, $\Delta$t can be set to 0.9 sec to 10 sec. This mechanism creates a practical and clear distinction between an 'in-range' and an 'out-of-range' patient for a period $\Delta$t, which is long enough for a user to see and act on the indication.

Figure 24:
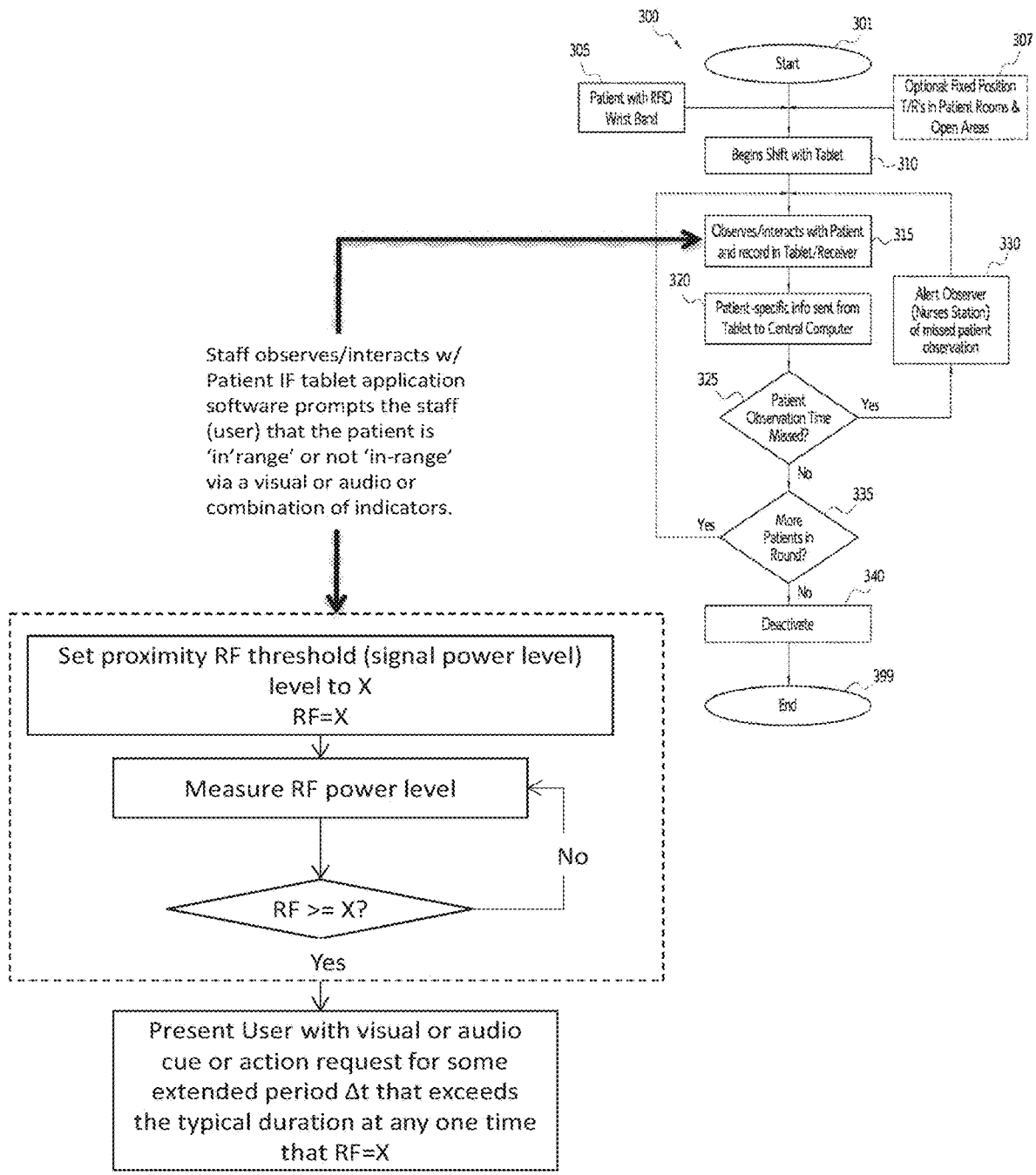
FIG. 24 is a flow chart illustrating the process from FIG. 3a that is followed by an observer using an electronic patient monitoring system showing where an electronic patient monitoring system and decision making process can be implemented in the process, in accordance with an embodiment of the disclosed subject matter.

FIG. 24 is a flow chart illustrating the process from FIG. 3a that is followed by an observer using an electronic patient monitoring system showing where an electronic patient monitoring system and decision making process can be implemented in the process, in accordance with an embodiment of the disclosed subject matter. As in FIG. 22, in FIG. 24, the electronic patient monitoring system and decision making process used can also be the process shown in FIG. 21. As seen in FIG. 24, the process outlined in FIG. 21 can be implemented in block 315 to monitor and control the detection, observation and recording of patient-specific information.

FIG. 25 is a flow chart illustrating the process from FIG. 3b that is followed by an observer using an electronic patient monitoring system with GPS and inter-patient distance monitoring showing where an electronic patient monitoring system and decision making process can be implemented in the process, in accordance with an embodiment of the disclosed subject matter. As in FIGS. 22 and 24, in FIG. 25, the electronic patient monitoring system and decision making process used can also be the process shown in FIG. 21. As seen in FIG. 25, the process outlined in FIG. 21 can be implemented in block 315' to monitor and control the detection, observation and recording of patient-specific information.

In an embodiment of the disclosed subject matter, a system including a central computer configured to store and execute program code to monitor and track observations of one or more patients assigned to one or more observers within a predetermined time interval; an observer transmitter/receiver (T/R) module configured to be attached to or carried by each of the one or more observers, store and execute program code to detect a proximity signal that exceeds a threshold level from an assigned patient, signal the observer of the detection, set a time to receive information about the patient, receive the information about the patient, and communicate the information about the patient to the central computer; a plurality of identification devices each configured to be attached to one of the patients and to communicate at least a unique proximity signal of the identification device and can include patient information to the observer T/R, each identification device including: a wristband comprising a section of a tamper resistant material having opposite ends with a plurality of spaced holes on each end; a beacon unit configured to emit a unique proximity signal associated with that beacon; a clasp configured to secure and hold the beacon unit and the wristband opposite ends via the plurality of spaced holes on each end together to form a closed loop, the clasp comprising a top portion adapted and configured to fit over and fixedly engage a bottom portion with a plurality of spaced pins on a top of the bottom portion and a pair of non-retractable slides positioned in apertures formed on opposite sides of the bottom portion and that fixedly engage openings formed in inside surfaces of opposite longitudinal side walls of the top portion; and at least one workstation configured to communicate with the central computer to receive information on the proximity of each patient to the observer T/R and observation check within the predetermined time interval.

The above system embodiment can also include the observer T/R module being further configured to perform a method including: activating a tablet for each observer as an active Bluetooth or Bluetooth low-energy T/R and receiving in each tablet a listing of pre-assigned patients and a patient observation time schedule; detecting the beacon signal from one of the pre-assigned patients, setting a time period in which to receive information of the detected patient and receiving in the tablet patient-specific information from the active Bluetooth or Bluetooth low-energy transmitter associated with the observed patient; sending the received patient-specific information from the tablet to the central computer including a time of observation of the one of the pre-assigned patients; determining whether any observation times in the schedule have been missed for any of the pre-assigned patients and, if so, sending alerts to at least a responsible observer and a nurses' workstation and logging the missed observation for each determined missed observation; determining whether there are more patients to be observed in the listing of pre-assigned patients and, if so, repeating steps b, c and d; and deactivating the tablet.

In an embodiment of the disclosed subject matter, a distributed system with multiple device processors communicatively connected to each other and at least one of the processors configured perform a computer-implemented method comprising: detecting a beacon signal in a first processor when at least one radio frequency (RF) signal received from a beacon equals or exceeds a predefined signal strength threshold, the beacon signal being associated with and unique to a single entity; determining a proximity to the beacon in the first processor based on the detected beacon signal strength; issuing an action request from the first processor based on the detected beacon signal being equal to or exceeding the predefined signal strength; waiting a predetermined time period to receive a response to the action request, regardless of subsequently-received beacon signals continuing to exceed or not exceed the predefined signal strength; receiving the response to the action request; and recording the received response to the action request.

In an embodiment of the disclosed subject matter, an identification device includes a wristband including: a section of a tamper resistant material having opposite ends, the opposite ends of the wristband having a plurality of openings formed therein adjacent to each of the opposite ends of the wristband and extending away from each end in along a common axis on the wristband; a clasp configured to secure and hold the wristband opposite ends together to form a closed loop, the clasp including: a bottom portion including a plurality of pins extended upwardly from and spaced longitudinally along a top of the bottom portion; a pair of non-retractable slides positioned in longitudinal grooves along opposite sides of the bottom portion; and a top portion adapted and configured to fit over and fixedly engage the pins on the top side of the bottom portion and the pair of non-retractable slides; and a beacon fixedly attached inside the clasp, the beacon configured to transmit a unique signal.

In an embodiment of the disclosed subject matter, an identification device including: a wristband including a section of a tamper resistant material having opposite ends, the opposite ends of the wristband having a plurality of openings formed therein adjacent to each of the opposite ends of the wristband and extending away from each end in along a common axis on the wristband; a clasp configured to secure and hold the wristband opposite ends together to form a closed loop, the clasp including: a bottom portion including a plurality of pins extended upwardly from and spaced longitudinally along a top of the bottom portion; a pair of non-retractable slides positioned in longitudinal grooves along opposite sides of the bottom portion; and a top portion adapted and configured to fit over and fixedly engage the pins on the top side of the bottom portion and the pair of non-retractable slides; and a beacon fixedly attached inside the clasp, the beacon configured to transmit a unique signal.

In an embodiment of the disclosed subject matter, a system including: a central computer including a processor configured to store and execute program code to monitor and track observations of patients received from at least one observer; an observer transmitter/receiver (T/R) module having a T/R processor, the module configured to be attached to or carried by each of the at least one observers and to store and execute program code in the T/R processor to monitor and track observations of patients within an observer's predetermined proximity to patient within a determined time interval, the program code when executed by a processor in the T/R module performs a method including: detecting a beacon signal when at least one signal received from a beacon exceeds a predefined signal strength; determining a proximity to the beacon based on the detected beacon signal strength; issuing an action request based on the detected beacon signal exceeding the predefined signal strength; waiting a predetermined time period to receive a response to the action request, regardless of subsequently-received beacon signals continuing to exceed the predefined signal strength; receiving the response to the action request; and recording the received response to the action request; an identification device configured to be attached to the patient and to communicate at least the beacon signal of the identification device and that can include patient information to the observer T/R, the identification device including: a wristband comprising a section of a tamper resistant material having opposite ends with a plurality of spaced holes on each end; a clasp configured to secure and hold the wristband opposite ends via the plurality of spaced holes on each end together to form a closed loop, the clasp comprising a top portion adapted and configured to fit over and fixedly engage a bottom portion and a pair of non-retractable slides; and a beacon fixedly enclosed by the clasp; and at least one workstation having a workstation processor, the at least one workstation configured to communicate with the central computer to receive information on the proximity of each patient to the observer T/R and observation check within the predetermined time interval.

As will be appreciated from the foregoing description the present disclosed subject matter provides an electronic patient monitoring system that includes a not easily removable patient identification and monitoring device affixed to a patient, an observer transmitter/receiver device to detect a beacon signal from the not easily removable patient identification and monitoring device when the beacon signal exceeds or equals a signal threshold value and hold open a window on the observer transmitter/receiver device for the observer to enter information on the patient, and a central computer system including, at least, a computer processor, communications components and system software to communicate with the observer transmitter/receiver device at specified/predetermined time intervals to receive observer- and patient-specific information.

The disclosed subject matter having been described in certain embodiments, it will be apparent to those skilled in the art that many changes and alterations can be made without departing from the spirit of the disclosed subject matter. Accordingly, Applicants intend to embrace all such alternatives, modifications, equivalents and variations in keeping therewith.

What is claimed is:

1. A system for monitoring a patient, the system comprising:
   a patient identification device, the patient identification device comprising a beacon configured to emit a radio frequency (RF) beacon signal, the beacon signal being associated with and unique to a single entity;
   an observer module configured to be operated by a user, the observer module comprising a receiver to detect the beacon signal;
   a processor in communication with the observer module, the processor including computer-program instructions, that, when executed by the processor, perform a computer-implemented method comprising:
   determining a beacon signal strength of the beacon signal received from the patient identification device;
   determining when the beacon signal strength of the beacon signal received from the patient identification device equals or exceeds a predefined signal strength threshold;
   determining that the observer module is in-range to the beacon based on the determined beacon signal strength;
   issuing an action request to the user when the beacon signal strength that was detected is equal to or exceeds the predefined signal strength threshold;
   waiting a predetermined time period to receive a response to the action request, regardless of subsequently-received beacon signals continuing to exceed or not exceed the predefined signal strength threshold;
   receiving a response to the action request from the user; and
   recording the response to the action request that was received.

2. The system of claim 1, wherein the processor issues the action request by issuing a visual or audio trigger.

3. The system of claim 1, wherein the processor determines the beacon signal strength by comparing a strength of the beacon signal against the predefined signal strength threshold.

4. The system of claim 1, wherein the processor receives a response to the action request by receiving a staff observation/interaction with the patient.

5. The system of claim 1, wherein the computer-implemented method further comprises setting the predefined signal strength threshold.

6. The system of claim 1, wherein the observer module is configured to be operated on a mobile phone or PDA held by the user.

7. The system of claim 1, wherein the patient identification device comprises a wristband of a tamper resistant material configured to be secured to the patient so that the patient identification device cannot be removed by the patient.

8. The system of claim 1, wherein the processor is remote from the observer module.

9. The system of claim 1, wherein the processor is wirelessly connected to the observer module.

10. The system of claim 1, wherein the computer-implemented method further comprises presenting the action request for an extended period of time that exceeds the predetermined time period.

11. The system of claim 1, wherein the computer-implemented method further comprises:
   determining whether the response to the action request that was received requires further action;
   if the response to the action request that was received requires one or more further actions, then initiating the one or more further actions, completing the one or more further actions, and recording results of the completed one or more further actions.

12. The system of claim 1, wherein the computer-implemented method further comprises:
   determining whether a second beacon signal has been received that exceeds the predefined signal strength threshold, then
   if a response to the action request was received and the second beacon signal exceeds the predefined signal strength threshold and the second beacon signal is associated with the patient, resetting the predetermined time period to run from a time of receipt of the second beacon signal that exceeds the predefined signal strength threshold;
   determining whether the predetermined time period to receive a response to a second action request has been exceeded;
   if the predetermined time period to receive a response to the second action request has been exceeded, then initiating one or more predefined warning protocols; completing the one or more predefined warning protocols; and recording results of the completed one or more predefined warning protocols.

13. A system for monitoring a patient, the system comprising:
   a patient identification device, the patient identification device comprising a beacon configured to emit a radio frequency (RF) beacon signal, the beacon signal being associated with and unique to the patient, wherein the patient identification device is configured to be secured to the patient so that the patient identification device cannot be removed by the patient;
   an observer module configured to be operated by a user, the observer module comprising a receiver to detect the beacon signal; and
   a processor in wireless communication with the observer module, the processor including computer-program instructions, that, when executed by the processor, perform a computer-implemented method comprising:
      determining when a signal strength of the beacon signal detected by the receiver of observation module equals or exceeds a predefined signal strength threshold;
      determining the user is in range of the patient based on the signal strength of the beacon signal that was determined;
      issuing an action request to the user based on the signal strength of the beacon signal that was detected being equal to or exceeding the predefined signal strength threshold;
      waiting a predetermined time period to receive a response to the action request, regardless of subsequently-received beacon signals continuing to exceed or not exceed the predefined signal strength threshold; and
      recording the response to the action request that was received.

14. The system of claim 13, wherein the processor issues the action request by issuing a visual or audio trigger.

15. The system of claim 13, wherein the processor measures a beacon signal strength to determine when the signal strength of the beacon signal detected by the receiver of observation module equals or exceeds the predefined signal strength threshold.

16. The system of claim 13, wherein the observer module is configured to be operated on a mobile phone or PDA held by the user.

17. The system of claim 13, wherein the patient identification device comprises a wristband of a tamper resistant material configured to be secured to the patient so that the patient identification device cannot be removed by the patient.

18. The system of claim 13, wherein the computer-implemented method further comprises presenting the action request for an extended period of time that exceeds the predetermined time period.

19. The system of claim 13, wherein the computer-implemented method further comprises: determining whether the response to the action request that was received requires further action; if the response to the action request that was received requires one or more further actions, then initiating the one or more further actions, completing the one or more further actions, and recording results of the completed one or more further actions.

20. A system for monitoring a patient, the system comprising:
   a wrist-worn patient identification device, the wrist-worn patient identification device comprising a beacon configured to emit a radio frequency (RF) beacon signal, the beacon signal being associated with and unique to the patient, wherein the wrist-worn patient identification device comprises a wristband of a tamper resistant material configured to be secured to the patient so that the wrist-worn patient identification device cannot be removed by the patient;
   a portable observer module configured to be operated by a user, the portable observer module comprising a receiver to detect the beacon signal; and
   a processor in communication with the portable observer module, the processor including computer-program instructions, that, when executed by the processor, perform a computer-implemented method comprising:
      determining when a signal strength of the beacon signal detected by the receiver of observation module equals or exceeds a predefined signal strength threshold;

determining the user is in range of the patient based on the signal strength of the beacon signal that was determined;

issuing an action request to the user based on the signal strength of the beacon signal that was detected being equal to or exceeding the predefined signal strength threshold;

waiting a predetermined time period to receive a response to the action request, regardless of subsequently-received beacon signals continuing to exceed or not exceed the predefined signal strength threshold; and recording the response to the action request that was received.

* * * * *